United States Patent
Orwar et al.

(10) Patent No.: US 12,012,578 B2
(45) Date of Patent: Jun. 18, 2024

(54) CELL PRINTING UTILIZING RECIRCULATING FLUID FLOWS

(71) Applicant: Fluicell AB, Gothenburg (SE)

(72) Inventors: Owe Orwar, Hovås (SE); Alar Ainla, Cambridge, MA (US); Gavin David Michael Jeffries, Gothenburg (SE); Shijun Xu, Västra Frölunda (SE)

(73) Assignee: Fluicell AB, Molndal (SE)

( * ) Notice: Subject to any disclaimer, the term of this patent is extended or adjusted under 35 U.S.C. 154(b) by 271 days.

(21) Appl. No.: 16/774,453

(22) Filed: Jan. 28, 2020

(65) Prior Publication Data

US 2020/0165554 A1    May 28, 2020

Related U.S. Application Data

(63) Continuation of application No. PCT/IB2018/000961, filed on Jul. 27, 2018.
(Continued)

(51) Int. Cl.
  *C12M 3/00* (2006.01)
  *A61L 27/38* (2006.01)
  (Continued)

(52) U.S. Cl.
  CPC ............. *C12M 21/08* (2013.01); *A61L 27/38* (2013.01); *B29C 64/106* (2017.08);
  (Continued)

(58) Field of Classification Search
  CPC ..................................................... C12M 21/08
  See application file for complete search history.

(56) References Cited

U.S. PATENT DOCUMENTS

| 4,575,330 A | 3/1986 | Hull |
| 8,210,119 B2 * | 7/2012 | Gale ............. B82Y 30/00 |
| | | 118/256 |

(Continued)

FOREIGN PATENT DOCUMENTS

| WO | WO2006014460 A2 | 2/2006 |
| WO | WO2014132139 A2 | 9/2014 |
| WO | 2019197333 A1 | 10/2019 |

OTHER PUBLICATIONS

International Search Report and Written Opinion, International Patent Application No. PCT/IB2018/000961, dated Aug. 1, 2019.
(Continued)

*Primary Examiner* — Xiao S Zhao
*Assistant Examiner* — Nicholas J Chidiac
(74) *Attorney, Agent, or Firm* — Noréns Patentbyrå AB

(57) ABSTRACT

One aspect of the invention provides a system for dispensing and printing cells and particles. The system includes: (a) a flow confinement device; (b) a controller configured to generate a confined liquid volume outside the flow confinement device, wherein the confined liquid volume or materials contained in the confined liquid volume can be released to the environment by confined, modulated, and non-confined flow modes in arbitrary sequence and for arbitrary periods of time by said controller; (c) one or more liquids containing cells or cell constituents supplied into the confined liquid volume through the flow confinement device; (d) a substrate; and (e) a system configured to position the flow confinement device in 3D space and, therefore, the confined liquid volume to be positioned relative to the substrate, such that the confined liquid volume and contents, can interact with the substrate.

17 Claims, 27 Drawing Sheets

Related U.S. Application Data

(60) Provisional application No. 62/538,272, filed on Jul. 28, 2017.

(51) Int. Cl.
  *B29C 64/106* (2017.01)
  *B29C 64/321* (2017.01)
  *B29C 64/386* (2017.01)
  *B33Y 10/00* (2015.01)
  *B33Y 50/00* (2015.01)
  *B33Y 70/00* (2020.01)

(52) U.S. Cl.
  CPC .......... *B29C 64/321* (2017.08); *B29C 64/386* (2017.08); *B33Y 10/00* (2014.12); *B33Y 50/00* (2014.12); *B33Y 70/00* (2014.12)

(56) References Cited

U.S. PATENT DOCUMENTS

| | | | |
|---|---|---|---|
| 8,735,117 B2 | 5/2014 | Darling et al. | |
| 10,119,107 B2* | 11/2018 | Tavana | B29C 64/112 |
| 10,119,108 B2* | 11/2018 | Maggiore | B33Y 40/00 |
| 2007/0231458 A1 | 10/2007 | Gale et al. | |
| 2008/0145639 A1 | 6/2008 | Sun et al. | |
| 2011/0177590 A1 | 7/2011 | Clyne et al. | |
| 2012/0225435 A1 | 9/2012 | Seger et al. | |
| 2015/0018968 A1 | 1/2015 | Sun et al. | |
| 2015/0321152 A1* | 11/2015 | Ainla | B01D 67/0002 427/8 |
| 2016/0046078 A1 | 2/2016 | Sun et al. | |
| 2016/0068793 A1* | 3/2016 | Maggiore | B29C 64/227 435/289.1 |
| 2016/0083681 A1* | 3/2016 | Tavana | C12M 21/08 425/162 |
| 2017/0072628 A1 | 3/2017 | Sun et al. | |
| 2017/0157644 A1* | 6/2017 | Ainla | B05D 3/14 |

OTHER PUBLICATIONS

Billiet, T., et al., "The 3D printing of gelatin methacrylamide cell-laden tissue-engineered constructs with high cell viability", Biomaterials 35 (2014) 49-62.

Derby, B., "Printing and Prototyping of Tissues and Scaffolds", Science, vol. 338, Nov. 16, 2012, 921-926.

Fluicell, "The Biopen Microfluidic System, Highly Localized Superfusion Device for Advanced Single-Cell Experiments". http://fluicell.com/thebiopensystem/, downloaded May 5, 2017, 4 pages.

Koch, L., et al., "Skin Tissue Generation by Laser Cell Printing", Biotechnology and BioEngineering, vol. 109, No. 7, Jul. 2012, 1855-1863.

Kuo, C. K., et al., "Ionically crosslinked alginate hydrogels as scaffolds for tissue engineering: Part 1. Structure, gelation rate and mechanical properties", Biomaterials 22 (2001) 511-521.

Lee, K. Y., et al., "Hydrogel Formation via Cell Crosslinking", Adv. Mater. 2003, 15, No. 21, Nov. 4.

Pataky, K., et al., "Microdrop Printing of Hydrogel Bioinks into 3D Tissue-Like Geometries", Adv. Mater. 2012, 24, 391-396.

Tang, Z., et al., "Biomedical Applications of Layer-by-Layer Assembly: From Biomimetics to Tissue Engineering", Adv. Mater. 2006, 18, 3203-3224.

Xu, T., et al., "Complex heterogeneous tissue constructs containing multiple cell types prepared by inkjet printing technology", Biomaterials 34 (2013) 130-139.

Communication pursuant to Art. 94(3) EPC dated Jul. 12, 2023.

* cited by examiner

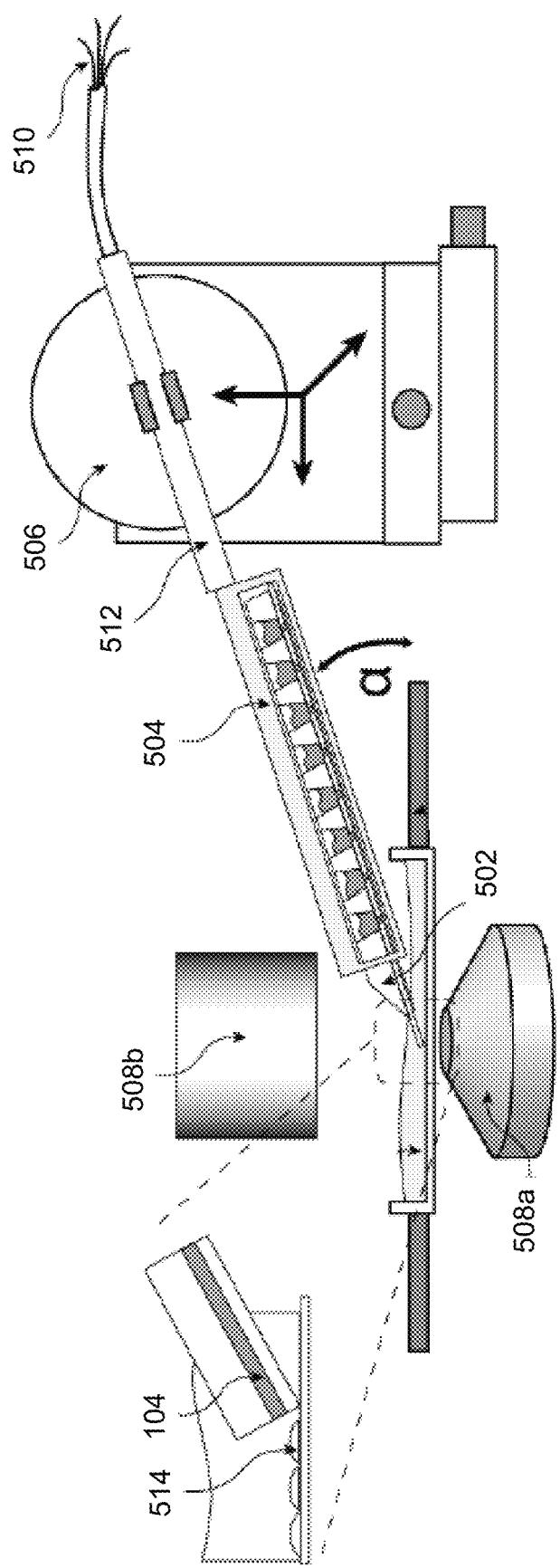

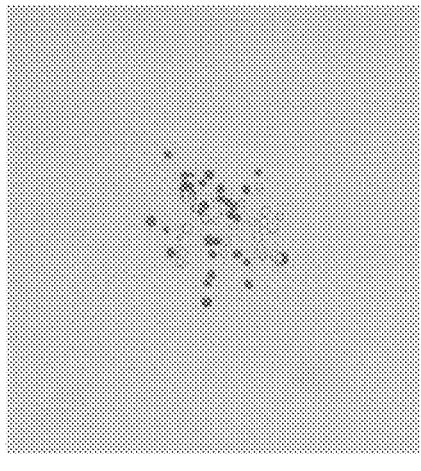
FIG. 16C
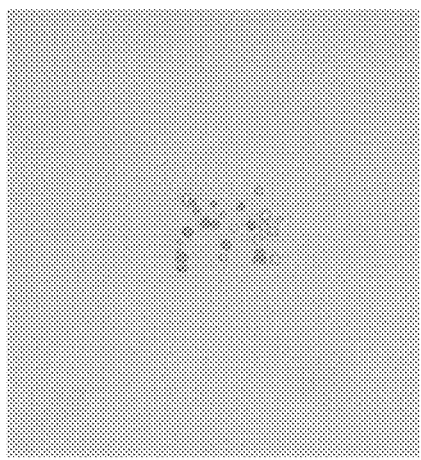
FIG. 16B
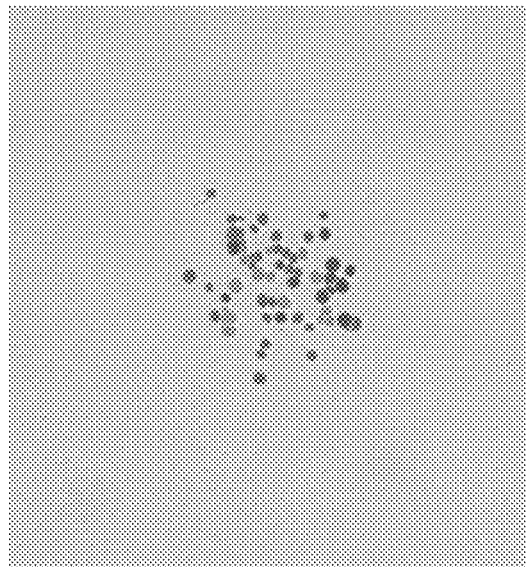
FIG. 16D
FIG. 16A

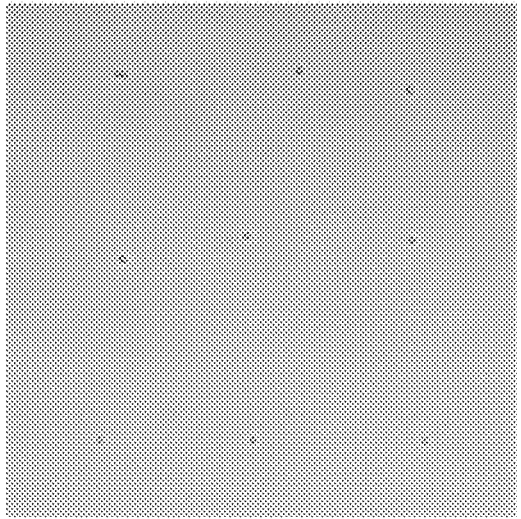
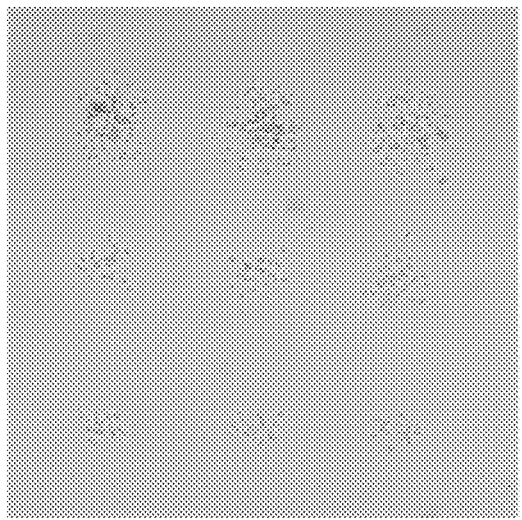
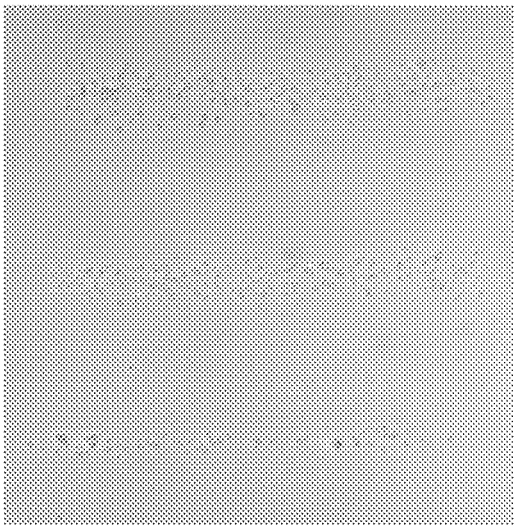
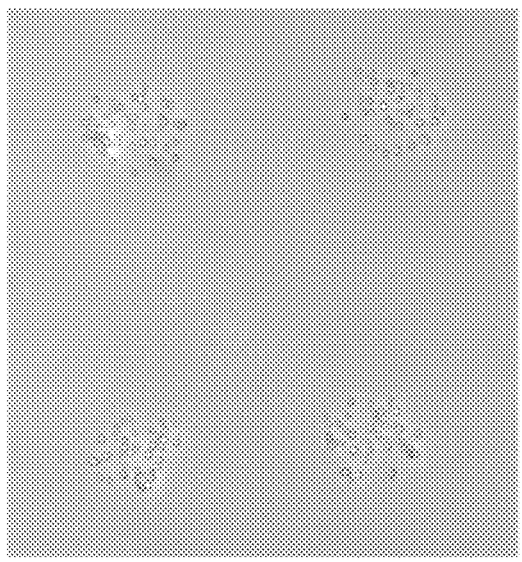
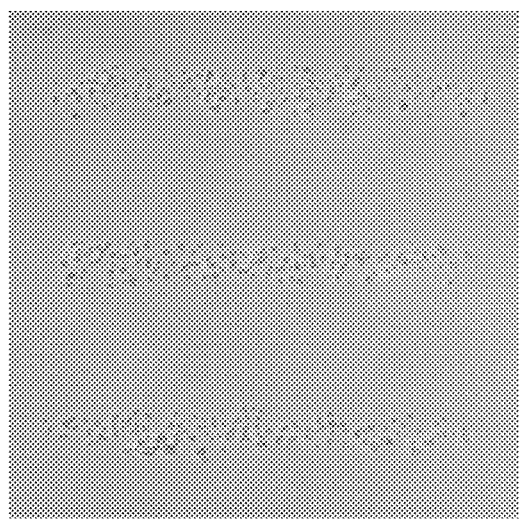
FIG. 18A
FIG. 18B
FIG. 18C
FIG. 18D
FIG. 18E

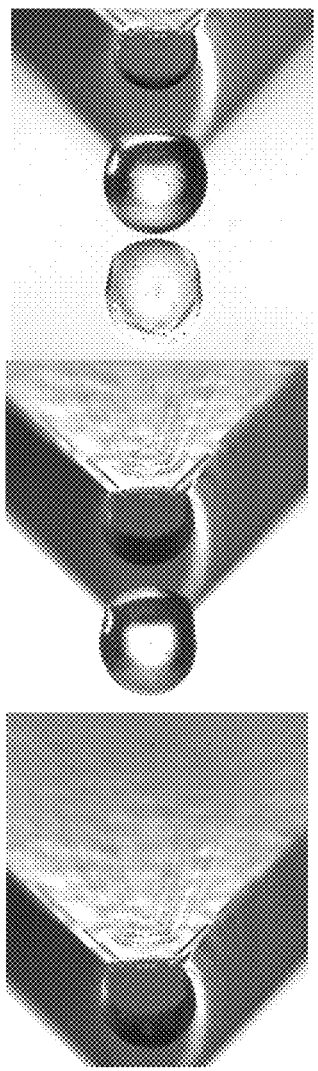
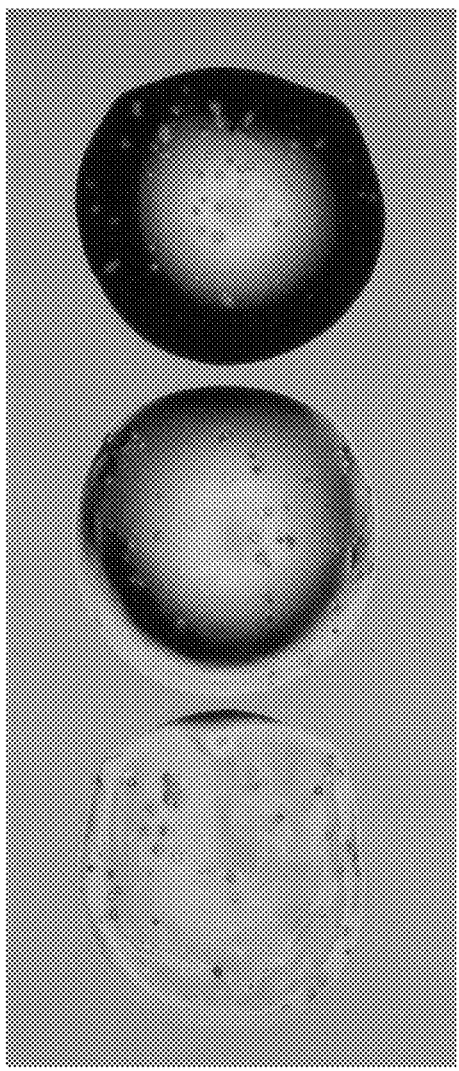

CELL PRINTING UTILIZING RECIRCULATING FLUID FLOWS

CROSS-REFERENCE TO RELATED APPLICATION

This application is a continuation under 35 U.S.C. § 120 of International Application No. PCT/IB2018/000961, filed Jul. 27, 2018, which claims the benefit of priority of U.S. Provisional Patent Application Ser. No. 62/538,272, filed Jul. 28, 2017. The entire content of this application is hereby incorporated by reference herein.

BACKGROUND OF THE INVENTION

Additive manufacturing (also known as "3-D printing") has been proposed for various biological applications. However, existing additive manufacturing technologies are dependent on substantially viscous extrusions that entrain and separate printed cells or on ink-jet style spraying of fluids.

SUMMARY OF THE INVENTION

One aspect of the invention provides a method including: (a) generating a recirculating flow from a flow confinement device over a substrate, the recirculating flow including a first liquid and a first plurality of suspended cells within the first liquid, the flow confinement device including a plurality of channels; and (b) switching between (a) and at least one of: continuing the recirculating flow over the substrate for a duration until a desired quanta of cells has been released from the flow confinement device; slowing, modulating, or discontinuing the recirculating flow over the substrate for a duration until a desired quanta of cells has been released from the flow confinement device; discontinuing the recirculating flow by altering pressure balance between one or several channels such that there is net positive pressure leading to that liquid and materials contained in said liquid are injected into the environment over the substrate and not flowing back to the flow confinement device for a duration until a desired quanta of cells has been released from the flow confinement device; discontinuing the recirculating flow by altering pressure balance between one or several channels such that there is no pressure difference between device and its surrounding leading to the recirculating flow being dispensed into the environment over the substrate and not flowing out of the flow confinement device and not flowing back to the flow confinement device for a duration until a desired quanta of cells has been released from the flow confinement device; and discontinuing the recirculating flow by altering pressure balance between one or several channels such that there is net negative pressure leading to that liquid and materials contained in said liquid are flowing back into the flow confinement device for a duration until a desired quanta of cells has been removed from the environment or the substrate back into the flow confinement device. Steps (a) and (b) are continued for an arbitrary period of time.

This aspect of the invention can have a variety of embodiments. The cells released from the flow confinement device can be deposited on a substrate. The cells released from the flow confinement device can be deposited on and adhere to a substrate.

One or several cell types can be deposited or printed to a substrate to create patterns of biological cell structures in 2D or 3D. The patterns of cell structures in 2D or 3D can be biological-tissue-like or biological-organ-like.

The cells released from the flow confinement device can be deposited to a first location on the substrate, and then can be moved by the flow confinement device to another location.

The cells released from the flow confinement device can be deposited to a first location on the substrate, and then removed by flow confinement device.

The substrate can be translated in 3D relative to the flow confinement device using an electronically controlled positioning device.

The method can further include assessing whether one or more of the cells attaches to the substrate. The assessing step can further include measuring surface coverage. Measuring surface coverage can include performing one or more selected from the group consisting of: visual observation, particle and object tracking from images, conductivity measurement, impedance measurement, fluorescence intensity measurement, optical density, phase retardation measurement, and acoustic wave sensing.

The method can further include: measuring the substrate after step (a); comparing this measurement to a reference value measured before step (a); and detecting whether the specified quantum of cells is present relative to the reference measurement.

The method can further include: repeating steps (a) and (b) with a further recirculating flow, wherein the further recirculating fluid contains a further plurality of suspended cells. The further recirculating fluid can be selected from the group consisting of: a cell binding medium, a membrane poration medium, an activating medium, a cell killing medium, and a releasing medium. The method can further include anchoring the attached cells to the substrate.

The suspended cells can attach to the substrate.

The specified quantum of cells can be a layer of adjacent cells having a specified threshold of coverage over a two-dimensional field.

The first liquid can be selected from the group consisting of: an aqueous solution, a volatile liquid, a polymer, a gel and media.

The first liquid can be media selected from the group consisting of: growth media, physiological media, selective media, differential media, freezing media, binding media, cell ink media, cell glue media, surface protecting media, and transport media.

The substrate can be selected from the group consisting of: a plastic material, a glass material, other inorganic materials, organic materials, a biological material, a cell layer, multiple cell layers, biological tissue, tissue section, an organ, an internal organ, inner ear, tumor tissue, endocrine glands, cardiovascular tissue, hair, hair follicle, cornea, retina, printed cells, printed tissue, tissue construct, organic gels, inorganic gels, protein aggregates, collagen, and gelled extracellular matrix.

The quanta of cells being dispensed can be controlled by the cell concentration in the fluid flow, modulated by mixing of flows within the flow confinement device.

The recirculation zone size can be pulsed larger to exceed the flow confinement to modulate the cell deposition area and number of cells released.

The quanta of cells being dispensed can be controlled by the duration of the fluid flow modulated by mixing of flows within the flow confinement device.

The quanta of cells being dispensed can be controlled by the distance the flow confinement device is from the substrate.

The substrate can be translated in 3D relative to the fluid flow applicator using a motorized positioning device.

Another aspect of the invention provides a system for dispensing and printing cells and particles. The system includes: (a) a flow confinement device; (b) a controller configured to generate a confined liquid volume outside the flow confinement device, wherein the confined liquid volume or materials contained in the confined liquid volume can be released to the environment by confined, modulated, and non-confined flow modes in arbitrary sequence and for arbitrary periods of time by said controller; (c) one or more liquids containing cells or cell constituents supplied into the confined liquid volume through the flow confinement device; (d) a substrate; and (e) a system configured to position the flow confinement device in 3D space and, therefore, the confined liquid volume to be positioned relative to the substrate, such that the confined liquid volume and contents, can interact with the substrate.

Another aspect of the invention provides a method including using the system as described herein to deposit cells or cell constituents from the one or more liquids to a substrate.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIGS. 4A and 4B depict micro-flow printing using an approach where recirculation is always active or on. In FIG. 4A, recirculation flow is established and maintained on, and the microfluidic device is placed at a distance from the surface where the recirculating fluid flow and cells contained therein are not in contact with the underlying substrate. As shown in FIG. 4B objects such as cells or particles can be dispensed onto a surface at a given location by bringing the microfluidic device close to the surface such that the recirculation flow and cells or particles contained therein comes in physical contact with the underlying surface or substrate. If the cells have an affinity for the surface or if the recirculation flow velocity is reduced or both, cells will settle on the surface. The number of cells added to the surface can be controlled by controlling the concentration of cells in the recirculation flow (i.e. cell solution added to microfluidic cell reservoirs), the duration of recirculation flow contact, the distance to the surface or size or speed of the recirculation flow zone, as well as substrate surface properties as further discussed below. As shown in another non-limiting configuration, in FIG. 4B, patterns can be formed at various locations by repeating the stages from FIG. 4A, and it is feasible to move the device while in proximal distance to the surface, to write patterns of arbitrary geometries. This mode of printing can also be combined with non-recirculatory flow modes as presented above, to release predefined quanta of cells or particles close to or far away from a surface. In one embodiment cells contained in liquid media are printed onto surfaces covered by liquids, and in another non-limiting embodiment cells contained in a gel or other semisolid material are printed onto surfaces in air media. FIG. 4C depicts micro-flow printing with a pulsed approach where the recirculatory flow is on for periods of time and off for periods of time or, alternatively flow is pulsed to change the size or disengage recirculation. The number of cells added to the surface can be controlled by controlling the concentration of cells in the recirculation flow (i.e. cell solution added to microfluidic cell reservoirs), the duration of recirculation flow contact, the distance to the surface or pulsing rate, size or speed of the recirculation flow zone, as well as substrate surface properties as further discussed below. It is feasible to move the device while in proximal distance to the surface, to write patterns of arbitrary geometries. This mode of printing can also be combined with non-recirculatory flow modes as presented above, to release predefined quanta of cells or particles close to or far away from a surface. In one embodiment cells contained in liquid media are printed onto surfaces covered by liquids, and in another non-limiting embodiment cells contained in a gel or other semisolid material are printed onto surfaces in air media.

FIGS. 5A and 5B depict an exemplary arrangement of a print-head, a holding interface, and micromanipulator(s) according to an embodiment of the invention, and an image of an exemplary embodiment. FIG. 5B depicts an image of an exemplary embodiment.

FIG. 6A depicts cell deposition of various patterns of cell type 1. FIG. 6B depicts cell depositions of various patterns of cell of types 1 and 2. Each pattern contains only one cell type. FIG. 6C depicts cell depositions of various patterns of cell of types 1 and 2. Each pattern can contain cells of type 1, or 2, or a mix of 1 and 2. FIG. 6D depicts layered cell deposition of various 3D patterns of cell type 1. FIG. 6E depicts layered cell depositions of various patterns of cell of types 1 and 2. Each pattern contains only one cell type. FIG. 6F depicts layered cell depositions of various patterns of cell of types 1 and 2. Each pattern can contain cells of type 1, or 2, or a mix of 1 and 2.

FIG. 15A depicts *Saccharomyces cerevisiae* deposited in a physiological buffer using a recirculation flow above the surface. FIG. 15B depicts the depositing of an adjacent spot of *Saccharomyces cerevisiae*. FIG. 15C depicts an exemplary spot array of the same size using *Saccharomyces cerevisiae*.

FIGS. 16A-16D depict cell deposition of three separate aliquots into the same spot using *Saccharomyces cerevisiae* in a physiological buffer onto a Concanavalin A-coated glass surface. FIG. 16A depicts deposition of *Saccharomyces cerevisiae* cells from the first on-device well. FIG. 16B depicts deposition of *Saccharomyces cerevisiae* cells from the second on-device well into the same region as from the first well. FIG. 16C depicts deposition of *Saccharomyces cerevisiae* cells from the third on-device well into the same region as from the first and second well. FIG. 16D depicts an overlay of the three different labels onto the printed spot, demonstrating the mixture between the three separate aliquots.

FIG. 17A depicts a single cell array of *Saccharomyces cerevisiae* where the cell to be edited is highlighted with a ring around it. FIG. 17B depicts a single cell array of *Saccharomyces cerevisiae* where the ringed cell has been removed. FIG. 17C depicts a single cell array of *Saccharomyces cerevisiae*, where the ringed area has been redeposited with a new single cell.

FIGS. 18A-18E depict examples of cell deposition using *Saccharomyces cerevisiae* yeast cells that have been printed in a physiological buffer onto a Concanavalin A-coated glass surface. FIG. 18A depicts an exemplary spot array of printed *Saccharomyces cerevisiae* cells where the spots are of the same size. FIG. 18B depicts an exemplary spot array of printed *Saccharomyces cerevisiae* where the spots are of different sizes. FIG. 18C depicts an exemplary printed single-cell array of *Saccharomyces cerevisiae* cells. FIG. 18D depicts exemplary printed lines of *Saccharomyces cerevisiae* cells where the lines have the same width. FIG. 18E depicts exemplary printed lines of *Saccharomyces cerevisiae* where the lines have different widths.

FIG. 19A depicts an exemplary spot array of printed SH-SYSY cells where the spots are of the same size. FIG. 19B depicts an exemplary spot array of printed SH-SYSY cells where the spots are of different sizes. FIG. 19C depicts an exemplary printed single-cell array of SH-SYSY cells. FIG. 19D depicts exemplary printed lines of SH-SYSY cells where the lines have the same width. FIG. 19E depicts exemplary printed lines of SH-SYSY where the lines have different widths.

FIG. 20A depicts an exemplary spot array of printed MDA-MB-231 cells where the spots are of the same size. FIG. 20B depicts an exemplary spot array of printed MDA-MB-231 cells where the spots are of different sizes. FIG. 20C depicts an exemplary printed single-cell array of MDA-MB-231 cells. FIG. 20D depicts exemplary printed lines of MDA-MB-231 cells where the lines have the same width. FIG. 20E depicts exemplary printed lines of MDA-MB-231 where the lines have different widths.

FIG. 21A depicts and exemplary printed 4×4 spot array with spots of the same size and alternating between Cell type 1 and Cell type 2. FIG. 21B depicts an exemplary printed array of nestled stripes using Cell type 1 and Cell type 2. FIG. 21C depicts an exemplary printed cross and spot combination pattern using Cell type 1 and Cell type 2. FIG. 21D depicts exemplary printed enclosed regions of Cell type 1 using Cell type 2.

FIG. 22A depicts printed lines having different widths using Cell type 1, deposited in a gel matrix. FIG. 22B depicts printed spots having different sizes using Cell type 2, deposited in a gel matrix. FIG. 22C depicts printed layered lines using Cell type 1, deposited in a gel matrix. FIG. 22D depicts printed layered lines using Cell type 2, deposited in a gel matrix.

FIG. 23A-23D illustrates examples of varying cell ratios in each deposited spot using A431 Epidermoid carcinoma in a gel matrix. Cell type 1 is unlabeled A431 Epidermoid carcinoma. Cell type 2 is labeled A431 Epidermoid carcinoma. FIG. 23A depicts exemplary depositing of Cell type 1 in a gel matrix forming a cell embedded region. FIG. 23B depicts exemplary depositing of Cell type 1 and Cell type 2 in a gel matrix forming a mixed cell embedded region. FIG. 23C depicts exemplary depositing of Cell type 2 in a gel matrix forming a cell embedded region. FIG. 23D illustrates the resulting three deposited regions, each containing a different cell ratio.

DEFINITIONS

Figure 1A:
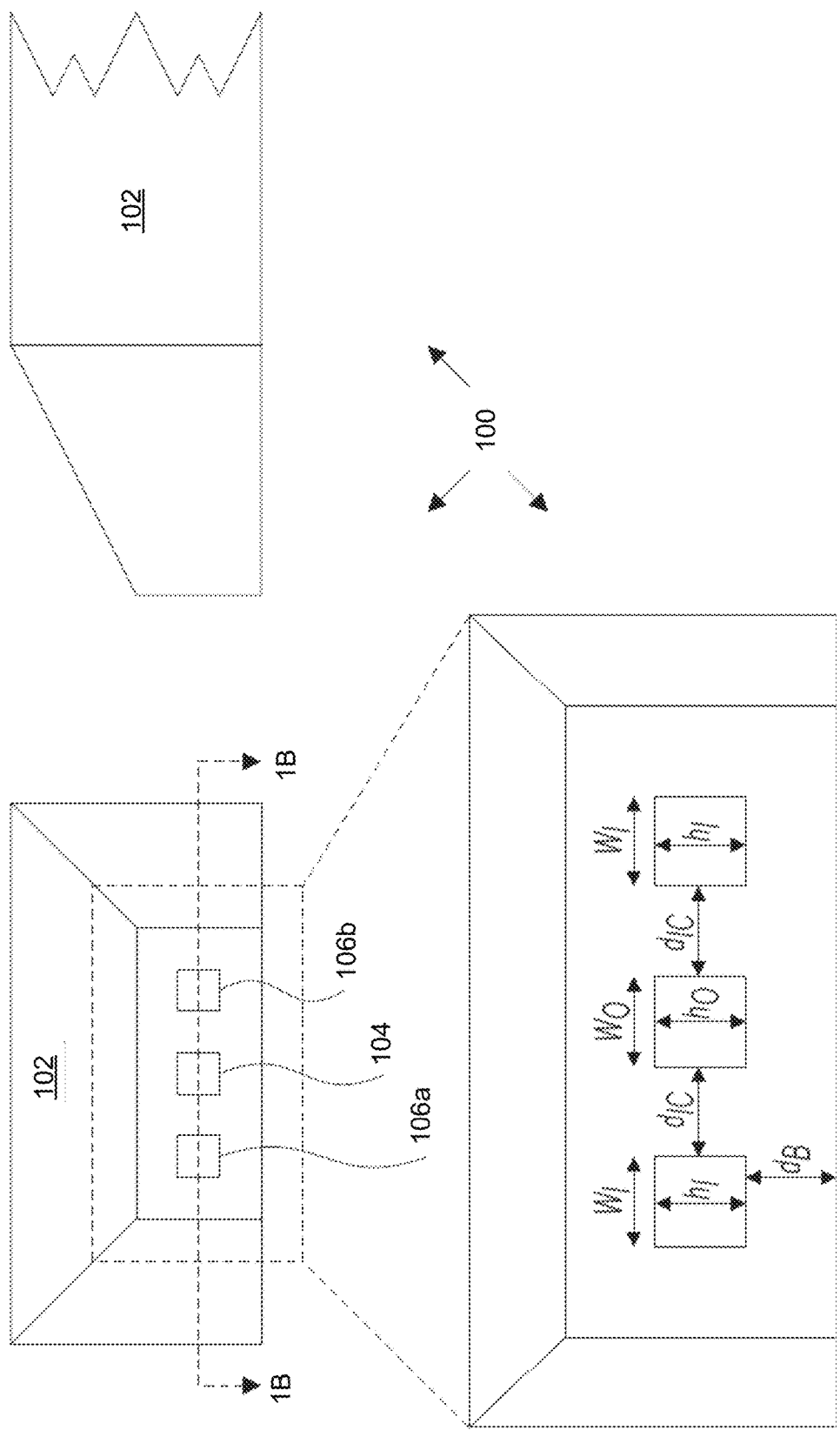
FIGS. 1A and 1B depict a schematic of a microfluidic print-head 100 according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "anchoring" refers to covalent bond formation between cells and a substrate, surface or other cells.

As used herein, the term "attachment" refers to non-covalent interactions between cells and a substrate, surface or other cells.

As used in the specification and claims, the terms "comprises," "comprising," "containing," "having," and the like can have the meaning ascribed to them in U.S. patent law and can mean "includes," "including," and the like.

As used herein, the term "substrate" refers to the area or the object in or on which cells are deposited. The substrate is to be construed broadly as the methods of the invention may be applied to a wide variety of different substrates. By way of non-limiting example, the substrate may be a surface, such as glass, which may or may not be functionalized. The substrate may be a volume element, such as a contained fluid or a gel. The substrate may also be cells of the same type or different from those deposited. In embodiments in which the substrate is a cell or cells, the cells may be suspended in a solution, attached to a surface or another object, or part of tissue, either in culture or from a living organism including a human.

Unless specifically stated or obvious from context, the term "or," as used herein, is understood to be inclusive.

Unless specifically stated or obvious from context, the term "recirculation" has the meaning of a fluid flow path exiting the device and returning to the same device.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Aspects of the invention provide microflow printing systems and methods for the controlled deposition of biological cells or cell constituents onto surfaces, including but not limited to the additive manufacturing of small-to-large cellular networks, tissues, organs, and other biological structures. In particular, embodiments of the invention can be used to create histologically complex cell structures in 2D and 3D. The microflow printing systems and methods comprising a flow confinement device and a controller configured to generate a confined liquid volume outside of the flow confinement device where the confined liquid volume can be modulated by said controller to include modulated and non-confined flow modes, as well as zero-flow modes, and where the controller can be used to switch between any flow modes in arbitrary sequence, for arbitrary periods of time; one or more media containing cells or cell constituents supplied into the confined or modulated liquid volume through the flow confinement device; a positioning system configured to position the flow confinement device and thus the confined liquid volume relative to a substrate, such that confined or modulated liquid volume can interact with the substrate; or alternatively, the confined or modulated liquid volume can be positioned within a predefined volume element in no contact with a surface.

In some embodiments, methods of cell deposition may be carried out under the control of a preprogrammed flow controller. In various embodiments, the system may further comprise a cell concentration measuring device for measuring cell deposition. In various embodiments, the preprogrammed flow controller may be programmed to assess whether a predefined number of cells are correctly located on the substrate. The feature of various embodiments by which parameters of the method are adjusted based on information collected over the course of the method is termed "feedback".

In various embodiments, the system may further comprise a device or method for measuring a cell property, such as a method for measuring protein expression, gene expression, metabolic markers, cell-cell interactions, ions, or other biological, physical or chemical properties of one or several cells in the various flow modes, including recirculatory flow.

Exemplary Fluid Flow Devices

Embodiments of the invention utilize fluid flows or recirculating fluid flows, generated at the tip of a flow confinement device, to achieve high resolution printing (e.g., with respect to both the lateral and axial position of the cells, deposition spot size for cell groupings, layer thicknesses, quantities of cells deposited, types of cells deposited, and the like). Although embodiments of the invention provide single-cell-deposition capabilities, embodiments of the invention can also deposit multiple cells at a time. For example, and without being bound by theory, Applicant believes that embodiments of the invention can reliably deposit layers having a thickness of less than two cells (e.g., less than about 500 µm, less than about 300 µm, less than about 200 µm, less than about 150 µm, less than about 100 µm, less than about 75 µm, less than about 50 µm, less than about 20 µm, less than about 10 µm, less than about 5 µm, and the like).

Flow confinement device comprises one or more channels of which some channels are configured as outlet channels, through which liquid leaves the device into an open volume and some channels are inlet channels, through which liquid is withdrawn from the open volume into the device. In some embodiment outlet channels and inlet channels are different channels. In some embodiments same channel can be intermittently switched to be outlet channel and an inlet channel. Flow confinement device further comprises a controller, which controls the liquid flow, such that all liquid leaving from the device is returning eventually back into the device when in recirculatory mode. Outflow can reach a limited maximal distance from the outlet channel before returning into the inlet channel. This distance defines the size of the confined liquid volume. Therefore the liquid outflow can reach a substrate or a surface, if it is positioned closer than the critical dimension of the confined liquid volume. In some embodiments, the outflow can reach the substrate, such that the flow confinement device does not have a direct contact with the substrate. For reasons of clarity, the tip of the flow confinement device can, in some non-limiting applications, be in contact with the substrate.

In various embodiments, the device can reliably deposit single cells, and or groups of cells, with a lateral resolution on the order of a single cell (e.g., less than about 150 µm, less than about 100 µm, less than about 75 µm, less than about 50 µm, less than about 30 µm, less than about 20 µm, and the like). Various non-limiting examples of depositing single cells and groups of cells are illustrated at least in FIGS. 17A-23D.

Figure 1B:
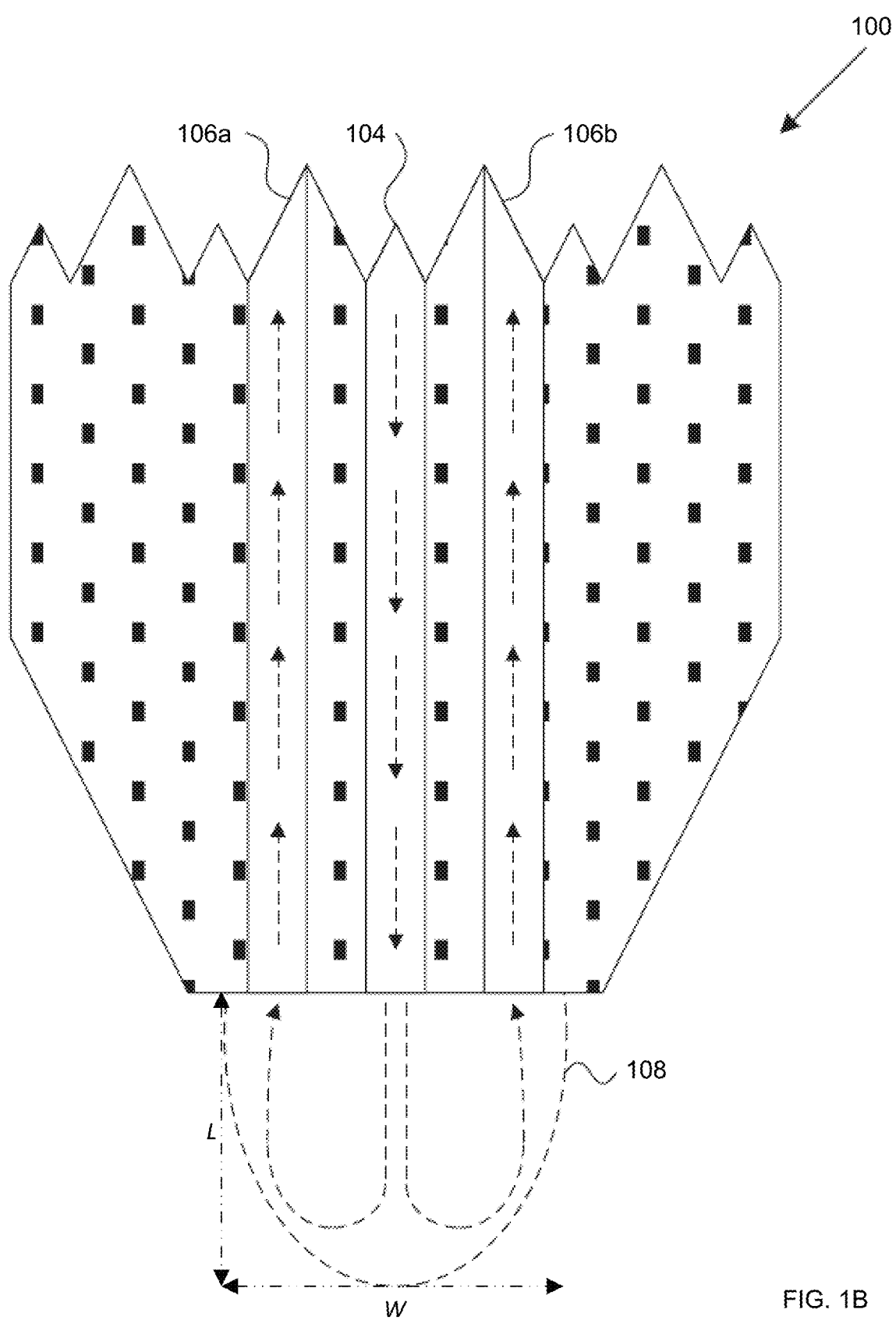

FIGS. 1A and 1B provide a schematic of recirculating fluid flow from a microfluidic print-head 100. Device 100 includes a substrate 102 that defines a microfluidic outlet channel 104 and two or more microfluidic inlet channels 106a, 106b.

As discussed herein, a microfluidic print-head 100 can be composed of one or more channels. For example, the microfluidic print-head 100 can include a total of about 10 total outlet and inlet channels. In some embodiments, the number of inlet channels is greater than the number of outlet channels. For example, the ratio of inlet to outlet channels can be 1:1, 2:1, 3:1, 4:1, 5:1 and the like. In some embodiments, the number of outlet channels is greater than the number of inlet channels. For example, the ratio of outlet to inlet channels can be 1:1, 2:1, 3:1, 4:1, 5:1 and the like.

Channels 104, 106 can, in some embodiments, be parallel to each other as depicted. Channels 104, 106 can have variety of cross-sectional profiles. In the embodiment depicted, channels 104, 106 have square cross-sections with cross-sectional widths $W_O$ and $W_I$ and heights $H_O$ and $H_I$, respectively.

The openings of channels 104, 106 can be positioned in a variety of locations on the dispensing region 108. In some embodiments, the position of the channels 104, 106 is defined with respect to a cross-sectional dimension of the channels 104 and/or 106.

In one embodiment, an inter-channel distance $d_{IC}$ can be between about 0.05 and about 5 times a cross-sectional dimension of channels 104 and/or 106. For example, a ratio of $d_{IC}$ to $W_O$, $W_I$, $h_O$, and/or $h_I$ can be selected from the group consisting of: between about 0.05:1 and about 0.1:1, between about 0.1:1 and about 0.5:1, between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

In various embodiments, the distance $d_B$ from the bottom of the openings to the bottom of the substrate 102 can be between about 0.05 and about 5 times a cross-sectional dimension of channels 104 and/or 106. For example, a ratio of $d_B$ to $W_O$, $W_I$, $h_O$, and/or $h_I$ can be selected from the group consisting of: between about 0.05:1 and about 0.1:1, between about 0.1:1 and about 0.5:1, between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

Substrate 102 can be selected from a variety of materials. In some embodiments, the substrate is an optically transparent material such as glass, plastics, rubbers, elastomers, ceramics, metals, and the like. Exemplary materials include polydimethylsiloxane (PDMS), poly(methyl methylacrylate) (PMMA), polyethylene (PE), polystyrene (PS), polypropylene (PP), thermoplastic elastomer (TPE) and the like.

A dispensing region 108 can be located on the exterior of substrate 102. Each of channels 104, 106 can include an opening on the dispensing region 108. In operation, a fluid flows out of outlet channel 104 and gathers and circulates in the dispensing region 108 before being withdrawn by inlet channels 106. An exemplary flow pattern is depicted in FIG. 1B.

As will be appreciated by one of ordinary skill in the art, the volume and dimensions of the fluid gathered in dispensing region 108 will vary as a result of a variety of parameters including the ambient pressure in an open volume in which the dispensing region 108 is placed, the flow rates and pressures in channels 104, 106, the fluid dispensed, the material of substrate 102, and surface tension between the dispensed fluid and objects that the dispensed fluid contacts. However, the dispensed fluid will often have a generally circular to generally elliptical shape.

The length L of the dispensed liquid can, in some embodiments, be between about 0.1 and about 10 times the cross-sectional width w of one or more of channels 104 and/or 106. For example, the ratio L:w can be selected from the group consisting of between about 0.1:1 and about 0.5:1, between about 0.5:1 and about 1:1, between about 1:1 and about 2:1, between about 2:1 and about 3:1, between about 3:1 and about 4:1, between about 4:1 and about 5:1, between about 5:1 and about 6:1, between about 6:1 and about 7:1, between about 7:1 and about 8:1, between about 8:1 and about 9:1, and between about 9:1 and about 10:1.

The width W of the dispensed liquid can, in some embodiments, be between about 1 and about 10 times the cross-sectional width w of one or more channels 104 and/or 106. For example, the ratio W:w can be selected from the group consisting of between about 1:1 and about 2:1, between about 2:1 and about 3:1, between about 3:1 and about 4:1, between about 4:1 and about 5:1, between about 5:1 and about 6:1, between about 6:1 and about 7:1, between about 7:1 and about 8:1, between about 8:1 and about 9:1, and between about 9:1 and about 10:1.

The flow rate through channels 104 and 106 can be optimized to achieve a desired result. In one exemplary embodiment having 10 μm square channels, flow rates ranging from 0.1 nl/second to 10 μl/second were achieved.

Channels 104, 106 can interface with fluid source through a variety of devices known to those of skill in the art including male/female connectors, tubing, wells, and the like. Various interfaces are described in U.S. Pat. No. 9,658,240.

Exemplary Cell Dispensation Scheme

The recirculating fluid flow can emerge and be withdrawn from a device as described above. In one embodiment, cells, cell fragments, subcellular organelles, particles, and the like are contained within this fluid, enabling controlled quanta of particles and/or cells to be dispensed to a solution and/or to a surface. The concentration of particles/cell in the flow can be determined from either the initial concentration as it entered the microfluidic device and/or an online monitoring scheme e.g. conductivity, impedance, fluorescence, phase retardation and the like.

FIGS. 2-4C depict non-limiting embodiments of a microfluidic print head, capable of varying, and modulating the re-circulation flow zone, as well as creating non-recirculatory flow modes at will by balancing fluid flow, via input and output pressure control, thus controlling cell dispensation. Channel exits are located at the tapered tip of the microfluidic print head to, among others, facilitate applicability, ease of positioning and visualization.

The non-limiting examples contained herein describe a 3-channel variant of the microfluidic print head. However, in principle, the device could contain fewer or several more channels, for example, 1-3 channels, 3-6 channels, 6-15 channels, 15-30 channels, 30-50 channels, 50-100 channels, 100-500 channels, 500-1000 channels, more than 1000 channels, and so on. These channels can be controlled in parallel, in sequence, in series, or a combination of such, to deliver several cell/particle suspensions independently or simultaneously.

Figure 2:
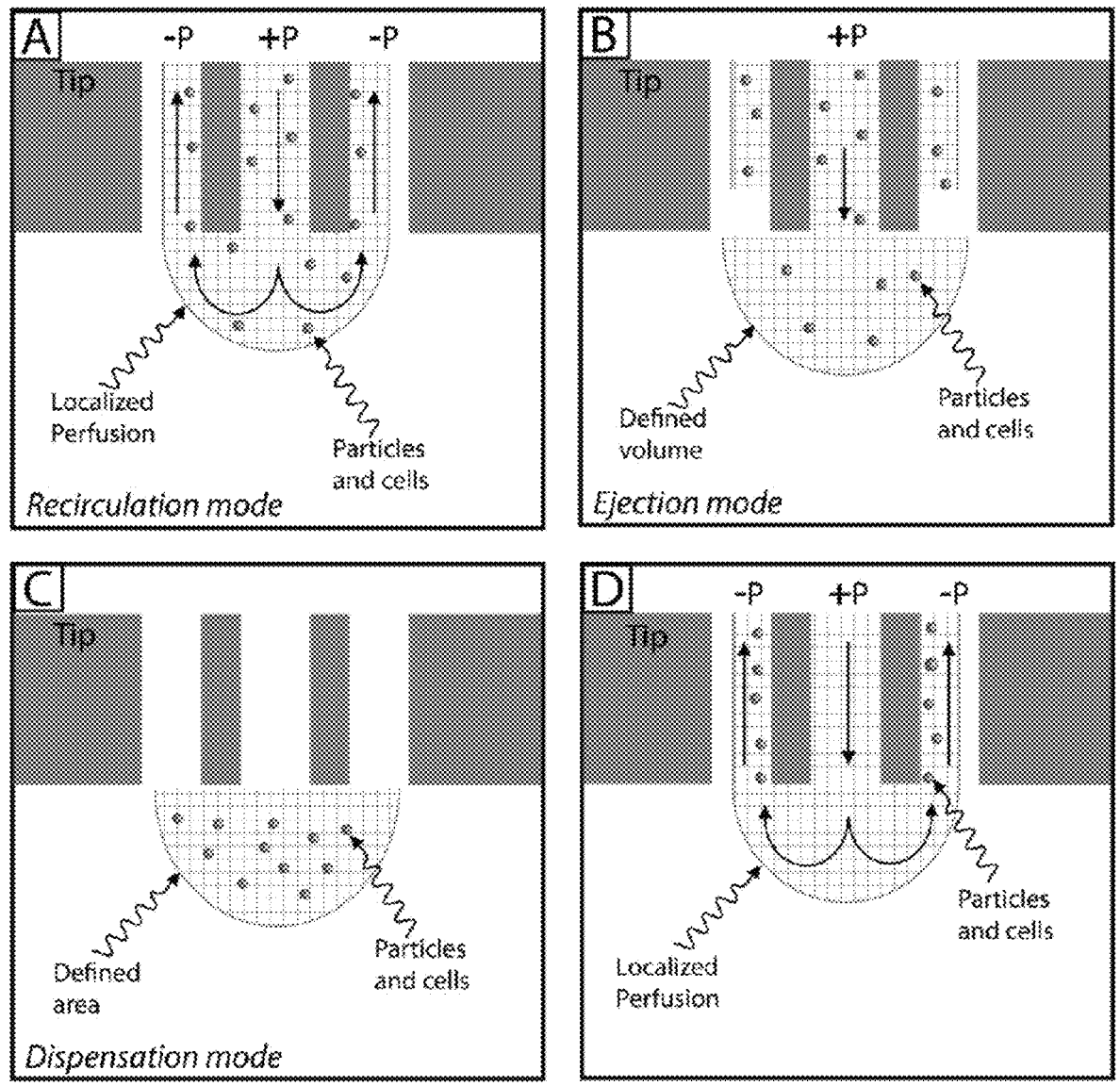
FIG. 2 depicts a non-limiting embodiment whereby cells can be dispensed through control of the individual channel pressures in a 3-channel device. This device can be toggled through the numerous presented modes; Recirculation, Ejection, and Dispensation, in FIG. 2A-C. Recirculation mode can be further utilized to clean isolate and select a region for sampling of cells and particles (indicated in FIG. 2D).

FIG. 2 depicts one embodiment whereby cells can be dispensed through control of the individual channel pressures in a 3-channel device. FIG. 2, Panel A illustrates a recirculation mode whereby the fluid flows from the central channel and back into the side channels. This is accomplished when both the positive pressure channel (+P) and the two negative pressure channels (−P) are engaged and in balance to maintain a recirculation flow zone as discussed above. Both the size of the recirculation zone and the speed of the fluid flow can vary depending on the applied pressures to each of the channels, the fluidic device layout and channel dimensions and geometry, fluid composition and application environment.

FIG. 2, Panels B and C demonstrate another embodiment, whereby a fluid aliquot is dispensed, then released, delivering a defined quanta of cells, coined the sample ejection mode and sample dispensation mode, respectively. First, as shown in FIG. 2, Panel B, lowering or disengaging the negative pressure in the two side channels, effectively switching off the vacuum, results in cells and or particles disconnecting from the inlet channels and beginning to be continuously introduced into the solution. In FIG. 2, Panel C, all channel pressures are lowered or disengaged, resulting in a defined volume of particles and/or cells in the solution and/or on a surface. It is feasible to move or translate the device in axial and lateral dimensions when in any of the flow modes shown in FIG. 2A-2C, to release cells into predefined volume elements and to write patterns of arbitrary geometries. In one embodiment cells contained in liquid media are printed onto surfaces covered by liquids, and in another non-limiting embodiment cells contained in a gel or other semisolid material are printed onto surfaces in air media.

FIG. 2, Panel D presents recirculation flow used as a sampling mode. Through implementation of a negative pressure in the two side channels, and switching the delivery fluid to one void of particles and/or cells previously introduced, cells and/or particles can be collected or sampled from the solution and/or surface, and withdrawn into the microfluidic print head. Non-limiting uses include: removing excess cells, sampling a predetermined cell and/or region. The sampled cell(s) can later be accessed through one of the print head reservoirs for further analysis. Thus, during cell printing or cell deposition, the printer head can be used in a write (add cells) and correct (sample or remove cells) fashion to ascertain that the correct cell network or organ design is achieved as demonstrated, for example, at least in FIG. 17A-17C.

The modes presented in FIG. 2 (recirculation mode, ejection mode, dispensation mode and recirculation mode for collection) can all be performed at individual predefined locations, or through the use of manual or electronically controlled manipulators, be applied multiple times to the same or multiple locations, for any desired period of time using the same or different fluids and flow conditions. Additionally, any of the different flow modes can be on during translation of the microfluidic flow print-head, and it is possible to switch between any of the different modes at will. The locations can be, but are not limited to, a volume element in a liquid/gel or solid environment, regions on a substrate surface, within a cell dish, within a solution reservoir, on an organism, or in air.

In all embodiments, the quanta of cells and/or particles dispensed from the microfluidic print head is defined by, among others, the following parameters: the concentration of cells/particles in the delivery fluid introduced into the sample reservoirs, the size of the recirculation zone (which in turn, as discussed above, is defined by pressure balance between the device inflow and outflow), and time in the three delivery modes, i.e., recirculation, ejection, and dispensation.

Figure 3:
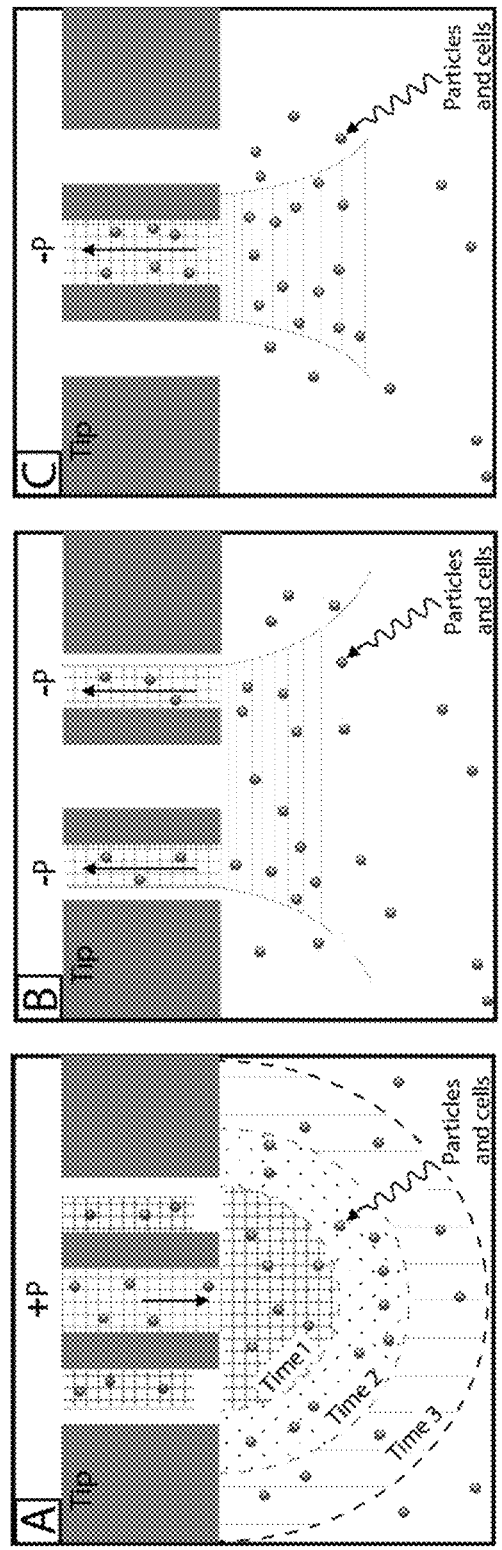
FIG. 3 depicts non-recirculatory flow modes according to an embodiment of the invention.

Further, non-recirculatory flow modes are exemplary extensions of the microfluidic print head capabilities. FIG. 3 introduces embodiments whereby the microfluidic print head is engaged in a mode that does not support recirculation. These can be envisaged as extensions to those introduced in FIG. 2. FIG. 3, Panel A describes an extension to the dispensation scenario, however utilizing the defined outflow from the channels, while also disengaging the side channels, to develop a timed exposure sequence, correlating to the distance to the channel outlet. FIG. 3, Panels B and C expand upon the recirculation mode for collection, presented in FIG. 2, Panel D. FIG. 3, Panels B and C introduce sampling schemes when there is no, or low, outflow from the device, using the negative-pressure side channels to uptake particles and/or cells and/or surrounding fluid into the microfluidic print head. FIG. 3, Panel C demonstrates a particular embodiment, whereby the flow direction of the central channel is reversed to facilitate directed uptake into the device.

Exemplary Micro-Flow Printing Approaches

Cell and/or particle deposition and patterning on a substrate can be accomplished using any of the device embodiments. Precise control of both inflow and outflow from the microfluidic print head enables multiple dispensation strategies to be achieved using the same device. Further extensions of the embodiments stem from varying the flow as a component of distance from the substrate.

Figure 4B:
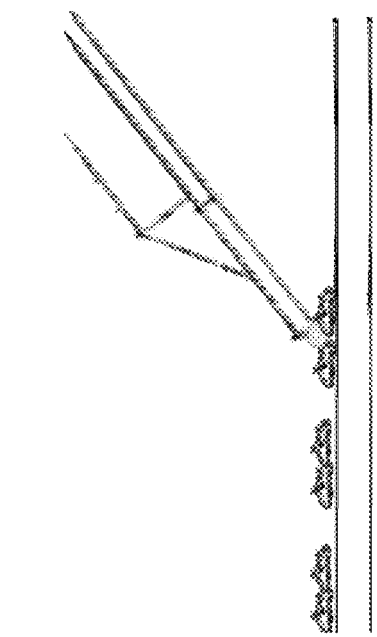
FIGS. 4A, 4B and 4C depict non-limiting schemes for depositing cells on a surface in various embodiments of the invention.
Figure 4A:
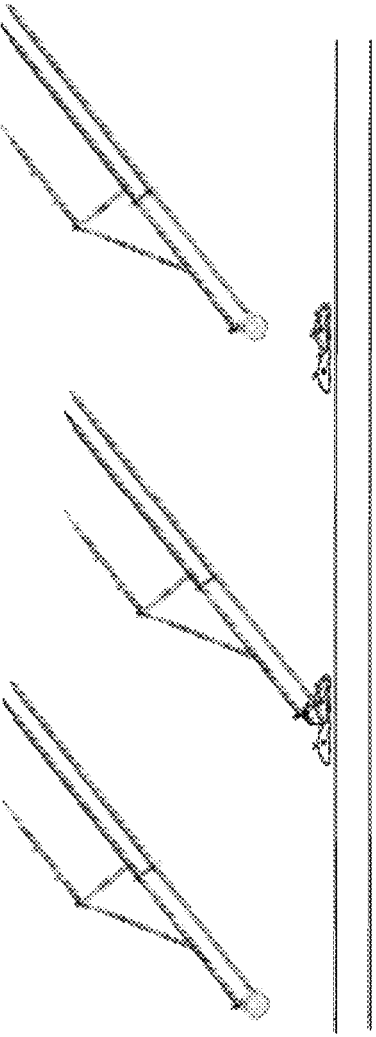
Figure 4C:
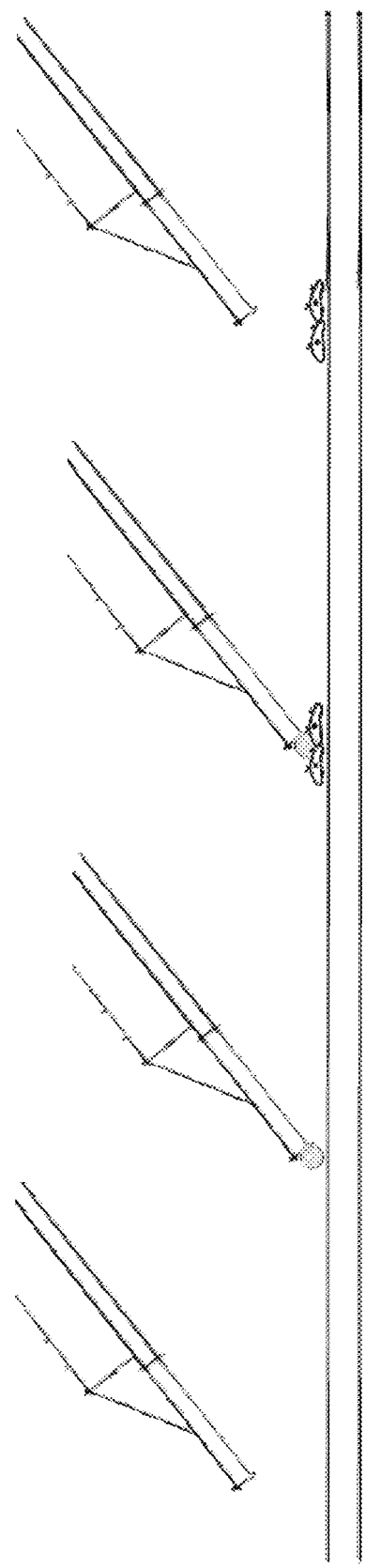

FIGS. 4A-4C highlight this approach as a form of microflow printing. FIG. 4, Panel A illustrates an always-on approach, whereby the recirculation flow is established and maintained during the course of a deposition. Cells and/or particles can be dispensed onto a substrate at a given location by controlling the duration of recirculation flow contact, the distance to the surface or size or speed of the recirculation flow zone.

In a non-limiting example, cells exit the recirculatory confined flow and attach to a surface or substrate when said flow, and cells contained therein are in physical contact with said surface or substrate, and the adhesion strength of the cell or cells to the surface is stronger than the hydrodynamic force created by the flow resulting in that the cell or cells are staying on the surface rather than following the flow back into the device.

The number of cells deposited to the surface can, additionally, be controlled by the concentration or number of cells per volume element in the cell solution added to the printer head reservoirs. Further, the number of cells deposited to the surface can, additionally, be controlled by properties of the surface.

Some surfaces have higher affinity for all, or certain cell types, and surfaces can be chemically or physically altered to support cell adhesion. Surfaces can also be coated with cell-adhesion-promoting molecules or materials, and can be patterned such that areas with high cell adhesion are surrounded by surfaces of low adhesion, and such structures can be made down to nanometer dimensions by people skilled in the art. The present invention can in all its embodiments be used with any type of standard or complex surface. Non-limiting examples of substrates include: a plastic material, a glass material, other inorganic materials, organic materials, a biological material, a cell layer, multiple cell layers, biological tissue, tissue section, an organ, an internal organ, inner ear, tumor tissue, endocrine glands, cardiovascular tissue, hair, hair follicle, cornea, retina, printed cells, printed tissue, and tissue construct. Furthermore, the substrate can be a three-dimensional structure, such as a 3-dimensional polymer network, a gel, a biological tissue, a biological organ, a printed three-dimensional cell structure, a three-dimensional solid state structure, a three-dimensional soft materials structure etcetera. FIG. 4, Panel B continues the strategy as patterns can be formed by repeating the stages from FIG. 4, Panel A at various locations. In one non-limiting embodiment cells are printed to a substrate when the recirculatory flow from the printerhead, and the cells contained therein are in physical contact with the substrate that is desired to be printed with cells, and that additionally there is adhesion or any other retention mechanism, including physical capturing, caging, and sequestration, as well as biological retention mechanisms, including protein-protein interactions, immunorecoginition, antigen-antibody binding, biotin-avidin binding, or adhesion proteins etcetera between cells and substrate that keeps the cells from being in the recirculation flow-thus being printed to the surface.

It is feasible to move the device while in proximal distance to the surface, to write patterns of arbitrary geometries, including histologically complex multi-cell structures in 3D. This mode of printing can also be combined with non-recirculatory flow modes as presented above to release predefined quanta of cells or particles close to or far away from a surface. In one embodiment, cells contained in liquid media are printed onto surfaces covered by liquids and, in another non-limiting embodiment, cells contained in a gel or other semisolid material are printed onto surfaces in air media.

FIG. 4, Panel C illustrates a pulsed approach, whereby the recirculation flow is pulsed to change the size, modulate or disengage the recirculation flow. Cells and/or particles can be dispensed onto a substrate at a given location by controlling the duration of recirculation flow contact, the distance to the surface, the pulsing rate, or size and speed of the recirculation flow zone. The number of cells deposited to the surface can, additionally, be controlled by the concentration or number of cells per volume element in the cell solution added to the printer head reservoirs. The non-limiting approach displayed in FIG. 4, Panel C describes a disengaged flow when the print head is away from the surface. The flow is then established and cell dispensation begins when the print head is brought close the substrate. Upon retraction away from the substrate the flow is once again disengaged.

It is feasible to move the device while in proximal distance to the surface, to write patterns of arbitrary geometries. This mode of printing can also be combined with non-recirculatory flow modes as presented above, to release predefined quanta of cells or particles close to or far away from a surface. In one embodiment cells contained in liquid media are printed onto surfaces covered by liquids, and in another non-limiting embodiment cells contained in a gel or other semisolid material are printed onto surfaces in air media.

Exemplary Disposable Microfluidic Print Head

Figure 10C:
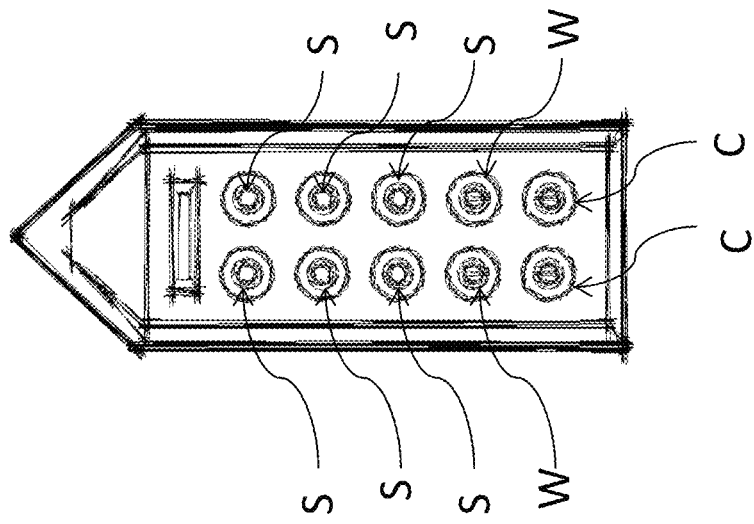
FIGS. 10A-10C depict three embodiments of a microfluidic print head, whereby some or all of the delivery fluids, wastes and or sampled fluids are housed within the device. 'S' denotes cell/particle/fluid reservoirs. 'C' denotes sampling reservoirs. 'W' denotes waste reservoirs.
Figure 10B:
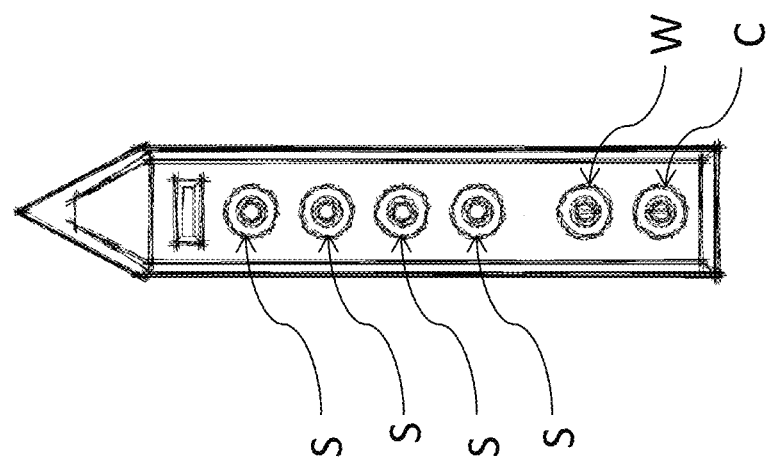
Figure 10A:
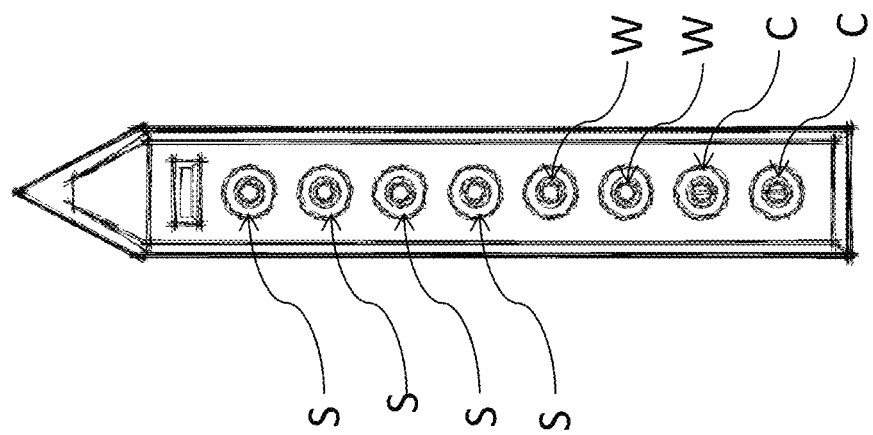

FIGS. 10A-10C depict three embodiments of a microfluidic print head, whereby some or all of the delivery fluids, wastes and or sampled fluids are housed within the device. FIG. 10A illustrates a four-fluid delivery device, with two additional reservoirs for waste collection and two reservoirs to house the collected fluid, in which particles and cells may have been carried. FIG. 10B illustrates a further embodiment where the number of waste reservoirs and sampling reservoirs has been reduced. FIG. 10C presents an additional embodiment, increasing the number of delivery fluid reservoirs.

Exemplary Micro-Organization Printing

Figure 7:
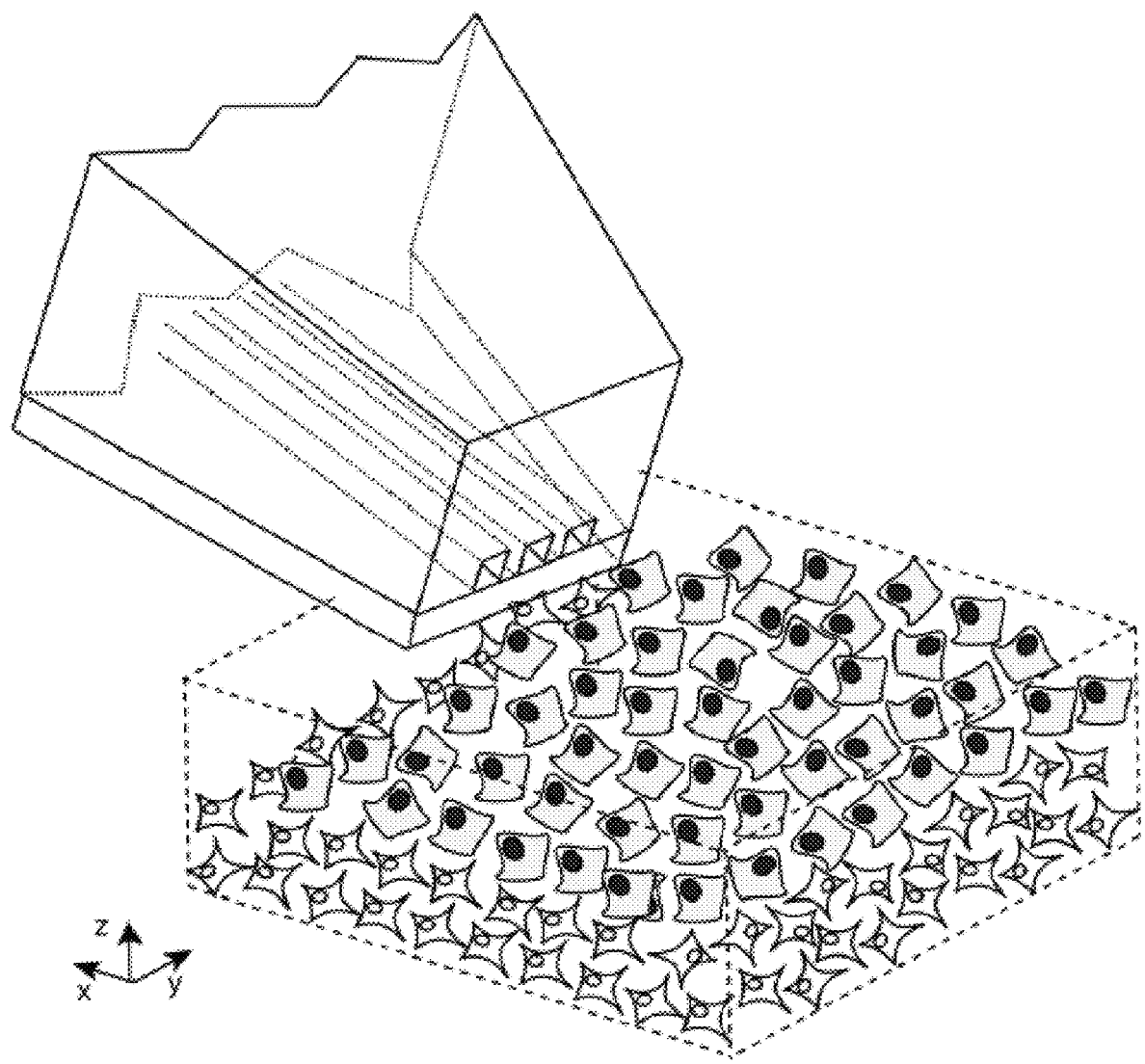
FIG. 7 depicts a visualization of a 3D structured, layered deposition of cells, of various cell types and sizes.
Figure 8:
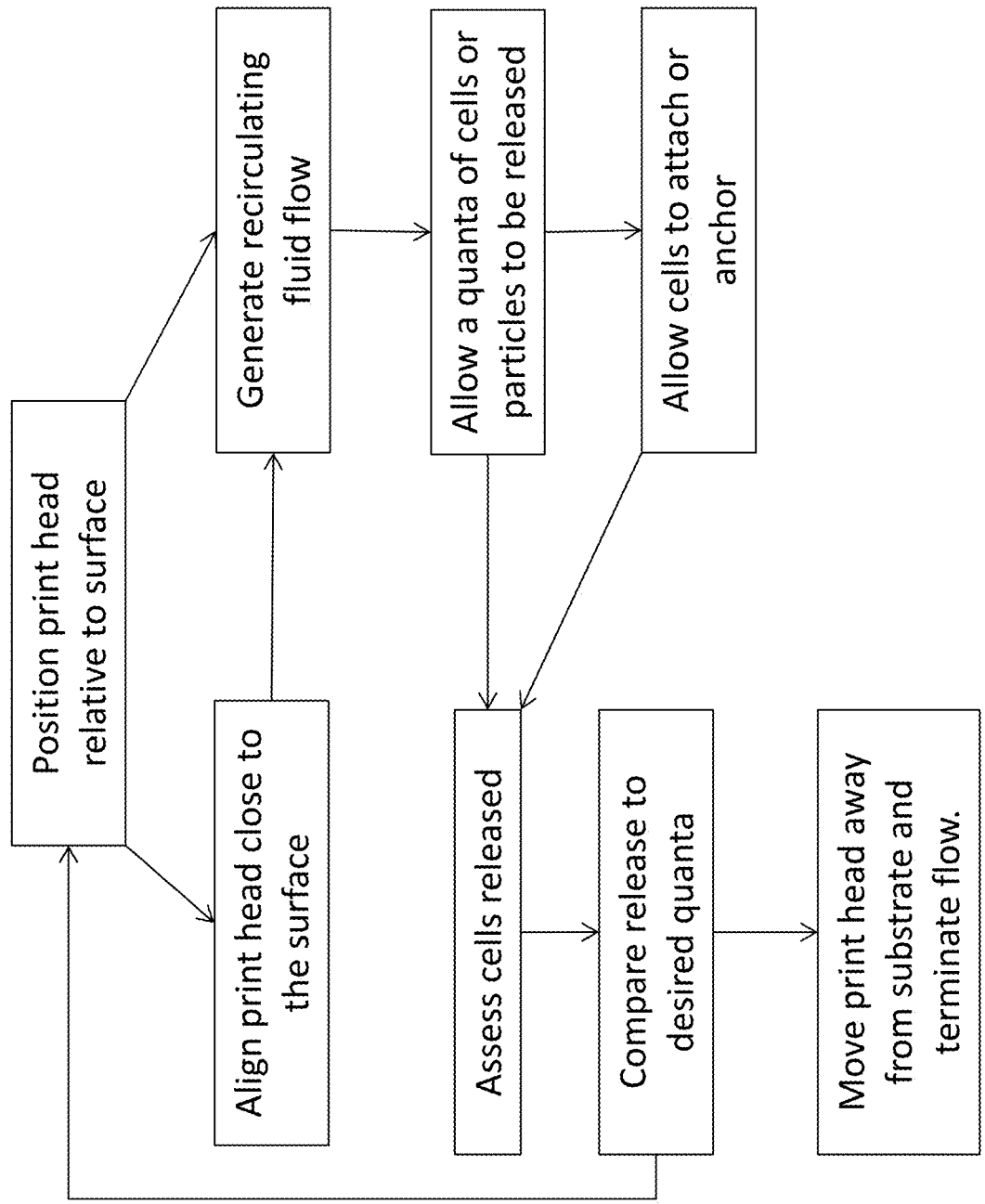
FIG. 8 depicts a cell deposition method using a recirculating fluid print head according to an embodiment of the invention.
Figure 11A:
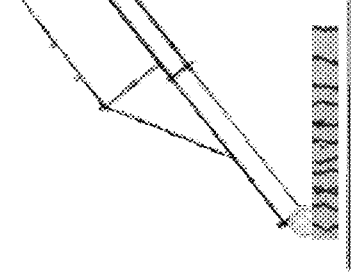
FIGS. 11A-11D depict the formation of a retina-like cell stack according to an embodiment of the invention, by patterning the desired cell type and density in a 3D manner.
Figure 11B:
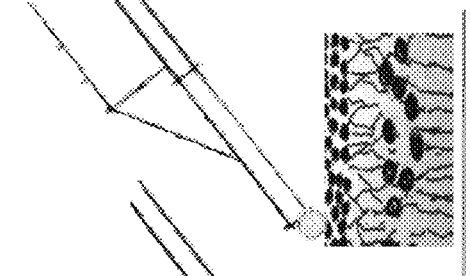
Figure 11C:
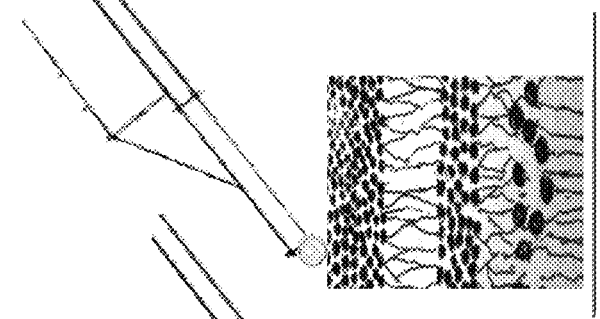
Figure 11D:
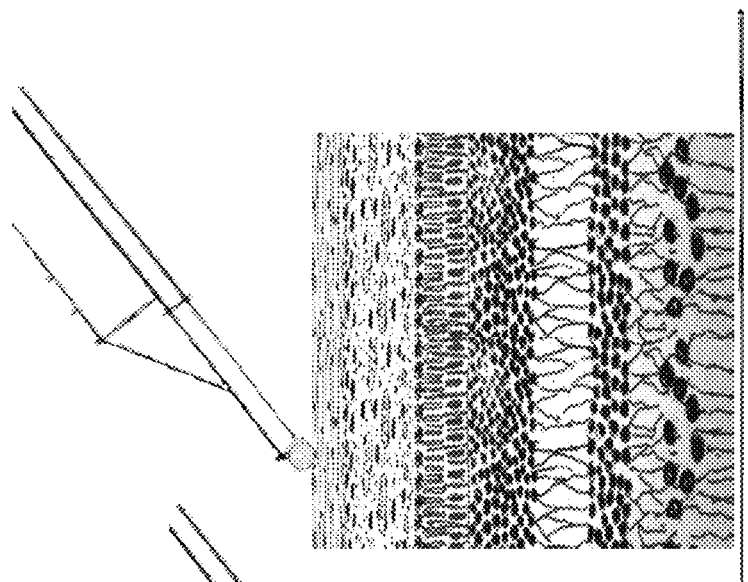

Higher-ordered structures can be assembled using the microfluidic print head via sequential cell(s) deposition onto patterned substrates and subsequent cell layers. The utility of this approach can be to construct organs or organ-like sections. Cell pattering strategies as those presented in FIG. 6 and FIG. 7, can wholly or partially be implemented to deposit cells in a layer by layer approach or a regional island deposition approach in which single or groups of cells are inserted into an existing natural or artificial tissue or organ or any other structure as described in more detail elsewhere in this text. One example of regional island deposition could be grafting of insulin-secreting beta cells into predetermined 3D (xyz) coordinates in pancreatic tissue, or the insertion of a cancer cell or group of cancer cells with particular genomic or metabolic profile into a cancer tissue consisting of another cancer cell type into predetermined 3D (xyz) coordinates to create heterogenous tumor model in vivo as well as ex vivo. Inserting cells using the disclosed technology into living animals as well as to cultured tissue can be accomplished using stereotactic devices, microsurgery positioners, and be aided by a surgical microscope and endosurgery probe technology. A non-limiting example of a layered approach is presented in FIG. 11A-11D, forming a retina-like cell stack composed of the following cell layers: inner limiting membrane, nerve fiber layer, ganglion cell layer, inner plexiform layer, inner nuclear layer, outer plexiform layer, outer nuclear layer, external limiting membrane, layer of rods and cones, and retinal pigment epithelium. FIG. 11A illustrates a seeding or attachment layer deposition, which, in some circumstances, can be used to aid in the patterning and adhesion of the cell(s). FIGS. 11B and 11C demonstrate the sequential cell layer build-up. Depositing the desired cells in a defined sequence leads to a retina-like section presented in FIG. 11D.

Exemplary Flow-Switching Architectures

Figure 14:
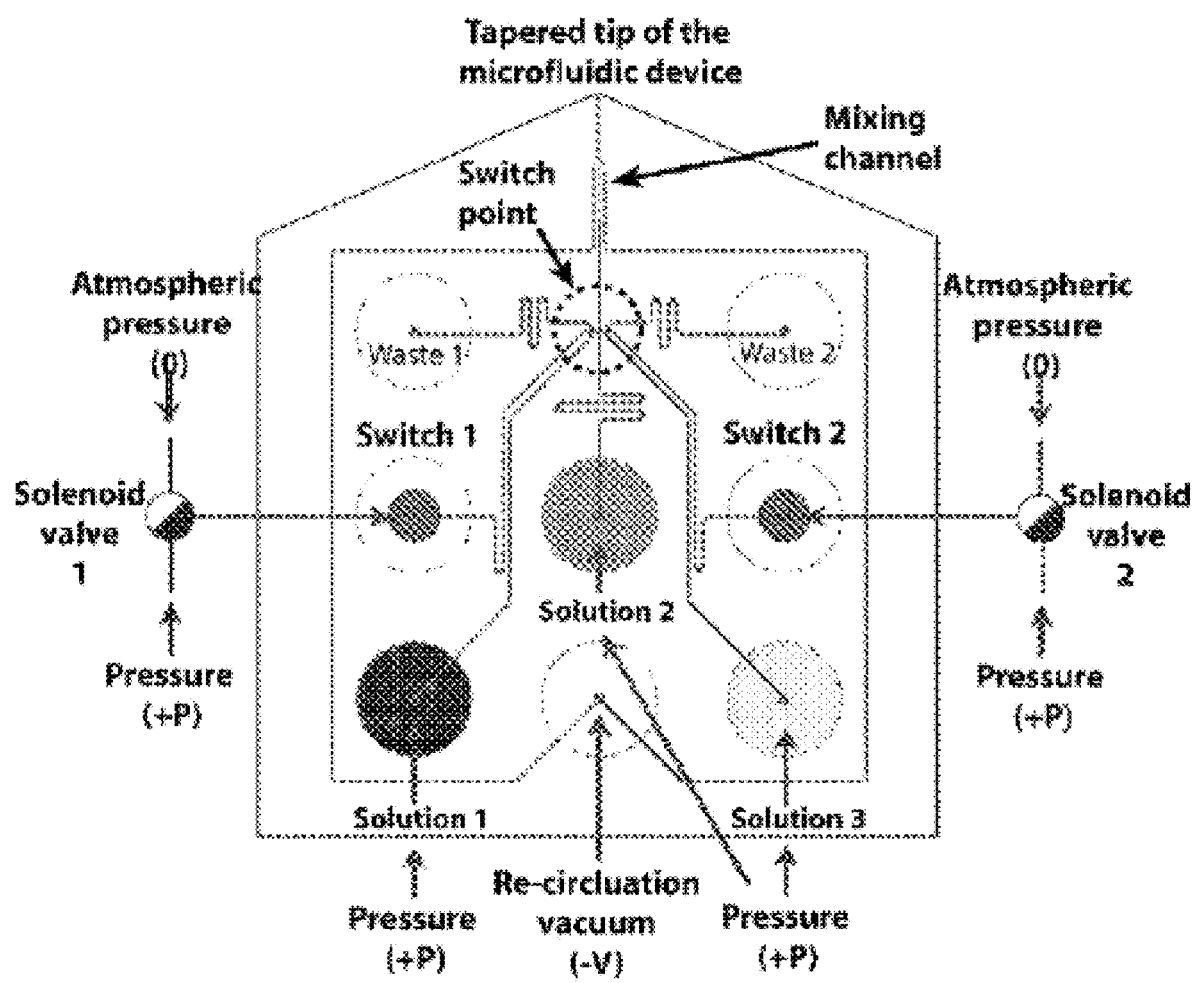
FIG. 14 depicts an example of a device capable of changing the composition of the re-circulation zone over time by multiplexing between several liquid inputs according to an embodiment of the invention.

FIG. 14 depicts a simple non-limiting example of a device capable of changing the composition of the re-circulation zone over time by multiplexing between several liquid inputs. Channel exits are located at the tapered tip of the microfluidic device to facilitate applicability. The device interface contains solution inputs, vacuum inputs, switching zones, four waste outputs, and one re-circulation output. The flow can be pressure driven. All solution inputs can be pressured at pressure +P, while vacuum lines can be pressurized to −P or to the atmospheric pressure (0). Pressures written below are deviations from atmospheric pressure, assumed to be 100 kPa, i.e. an applied pressure of 40 kPa represents a positive pressure over atmospheric pressure, having an absolute value of 140 kPa.

Pressure +P can, in some embodiments, range from about 0.1 kPa or 1 kPa to about 100 kPa. For example, pressure +P can be selected from the group consisting of: between about 1 kPa and about 10 kPa, between about 10 kPa and about 20 kPa, between about 20 kPa and about 30 kPa, between about 30 kPa and about 40 kPa, between about 40 kPa and about 50 kPa, between about 50 kPa and about 60 kPa, between about 60 kPa and about 70 kPa, between about 70 kPa and about 80 kPa, between about 80 kPa and about 90 kPa, and between about 90 kPa and about 100 kPa.

Pressure −P can, in some embodiments, range from about −0.1 kPa or −1 kPa to about −100 kPa. For example, pressure −P can be selected from the group consisting of: between about −1 kPa and about −10 kPa, between about −10 kPa and about −20 kPa, between about −20 kPa and about −30 kPa, between about −30 kPa and about −40 kPa, between about −40 kPa and about −50 kPa, between about −50 kPa and about −60 kPa, between about −60 kPa and about −70 kPa, between about −70 kPa and about −80 kPa, between about −80 kPa and about −90 kPa, and between about −90 kPa and about −100 kPa.

In various embodiments, the switching determines which of the solutions is directed towards the channel exit. In various embodiments, switching point and channel exit are separated by a mixing channel.

Flow-switching is further described in U.S. Pat. Nos. 9,126,197 and 9,671,366.

Exemplary Control Systems

The recirculating fluid flow confinement device can be readily positioned relative to an object of interest using either a manual positioning system, or through the implementation of an electronically controlled positioning device. The manual positioning system may include hydraulic, mechanical, or electrical (e.g., stepper motor) micromanipulators. These actuators can be arranged in one, two, three, four or greater directions. A non-limiting arrangement would be to place actuators to address a Cartesian coordinate system, 90 degree angle for each axis from the normal. A forth common axis would be at an approach angle in-line with the print head. The actuators can be independent from the stage, connected to the stage or differentially attracted, i.e. through a positional regulator. The electronically controlled positioning device may include, by way of non-limiting example, electronically controlled actuator, which could replace all or some of the actuators in a typical manual arrangement. Both manual and electronically controlled positioning devices can be direct drive, or be off axis driven, i.e. using a belt drive or a lead screws. The holding interface can be anchored to a single point, connected to a 1-axis positioning device, a 2-axis positioning device, a 3-axis positioning device, or a positioning device with greater degrees of freedom. The holding interface can in addition be mounted to a mobile platform over the substrate, allowing for ease of positioning over an object of interest, controlled by multiple on and off axis actuators. Additionally the actuator position can be temporarily or permanently fixed, and the object of interest can be positioned relative to the microfluidic print-head. The positioning of the object of interest can be achieved using either manual or electronically controlled actuators.

The electronically controlled position of both the print-head and the substrate can be achieved through on-demand control, e.g., through the use of a joystick or scroll wheel, and/or through the use of a computationally determined path. These paths can for example, be derived from a simple coordinate system, a design file, such as .stl (STereoLithography) CAD files, and/or through a relative feedback response, e.g., adapting to the changing position of cell propagation.

In various embodiments, the electronically controlled positioning device may be controlled via a manual input. By way of a non-limiting example, the manual input may include a joystick, scroll wheel, a touch screen and combinations thereof.

Referring now to FIG. 5A, microfluidic print-head 502 can be held by holding interface 504, which can be positioned with micromanipulator(s) 506 (e.g., under microscope 508a, 508b). Holding interface 504 can mechanically hold and support the microfluidic device 502 and control its position and angle towards the object of interest. The holding interface 504 can also interface an external pressure source to the wells of the microfluidic device 502 through tubing 510 to deposit material 514 through outlet channel 104. In an embodiment, the holding interface 504 has an elongated shape with extended rod 512, which can be connected to manipulator(s) 506, located close to the microscope 508a, 508b. Holder components under the device can also increase the minimum application angle (α). The full range of application angles can be from 0° to 90°. In many practical situations preferred range is in the range of 0° to 5°, 5° to 10°, 0° to 45°, and the like.

In another embodiment, the hold interface 504 has only a few components above the microfluidic device 502 near its tip. In some embodiments, the holding interface 504 can optionally have one or more electrical connectors to either the microfluidic device (if it has integrated electrodes) or to the liquid inside the wells.

In another embodiment, the holding interface 504 and the microscope are aligned to each other to monitor near to the tip of the microfluidic print-head.

In another embodiment, the holding interface contains additional components for interfacing to auxiliary fluidic sources, these can be either interfaced directly via tubing, fluidic connector, or by attaching directly to the microfluidic print-head.

Figure 5B:
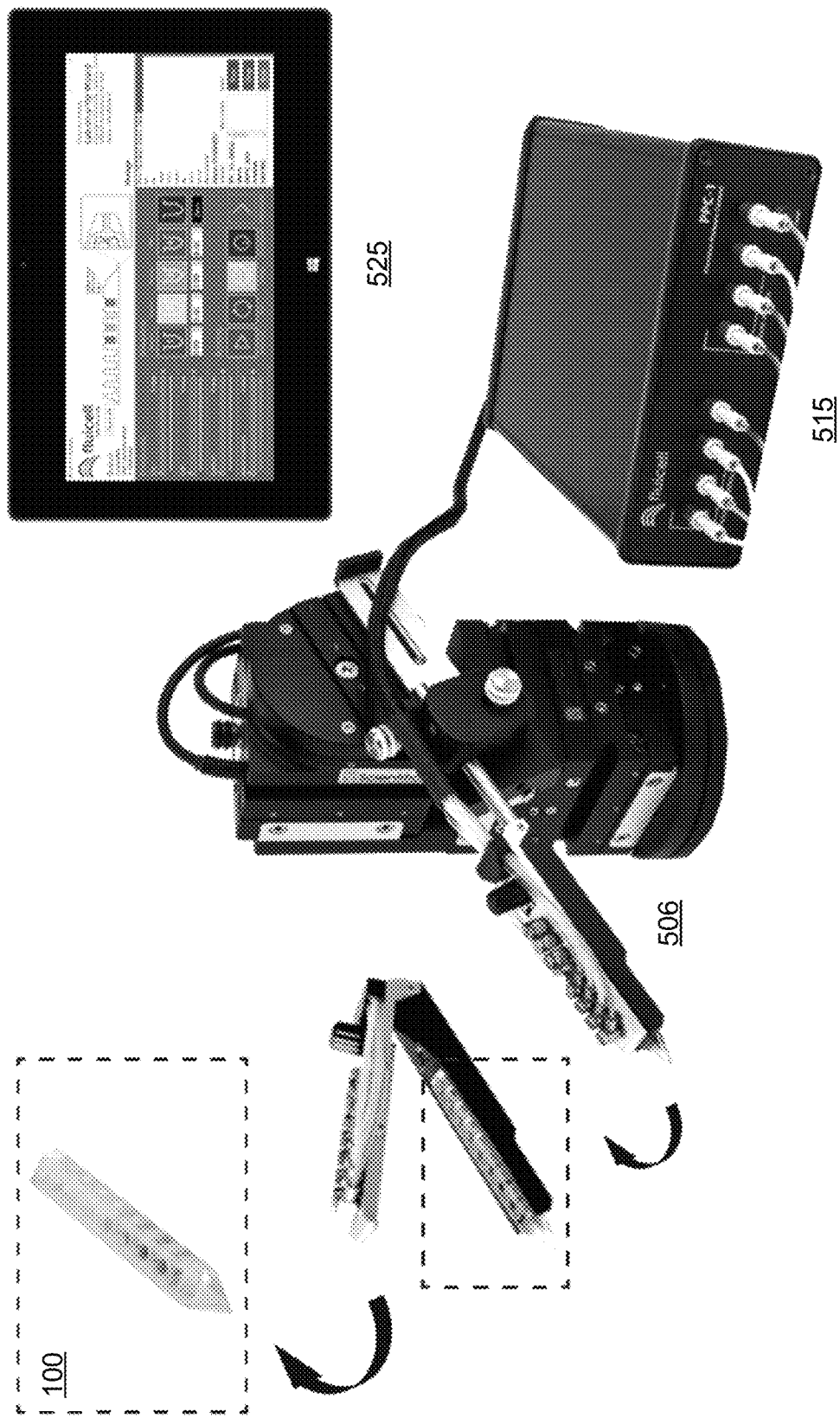

FIG. 5B depicts an exemplary embodiment of a system for controlling a microfluidic device available from Applicant under the BIOPEN® trademark.

In various embodiments, disposable microfluidic device 100 can deliver up to 4 different solutions. Utilizing hydrodynamic confinement, the delivered solution can be localized and rapidly switched. The microfluidic device can be made from a flexible medical grade elastomer material that, unlike glass pipettes, will not break upon contact with a hard surface. It can include 8 wells, e.g., 4 wells for containing solutions and 4 wells for collecting waste. Each well can contain up to 35 µl of solution.

Two levels of pneumatic pressure can be supplied by the pressure controller 515 and fast-solution-switching can be achieved through the use of miniature solenoid valves.

The holding interface 506 can include a pressure manifold to assure a closed system and to connect each solution reservoir of the microfluidic device 100 individually with the precision pressure controller 515. The microfluidic device 100 can be compatible with any standard type of micromanipulator such as, for example, those available under the PATCHSTAR™ trademark from Scientifica of Uckfield, United Kingdom.

A controller 525 can enable independent control of each pressure line and solution delivery. In various embodiments, the controller 525 may be programmed to carry out any embodiment of the methods of cell deposition described herein.

In some embodiments, the device further comprises a detector for assessing cell coverage. The various methods by which the detector may measure cell coverage are described below.

In various embodiments, the position of the substrate is translated manually and or by electronically controlled positioning device relative to a static microfluidic print head. In some embodiments the device further holds the print head in the optical path of a monitoring system such as a camera or microscope.

Figure 5C:
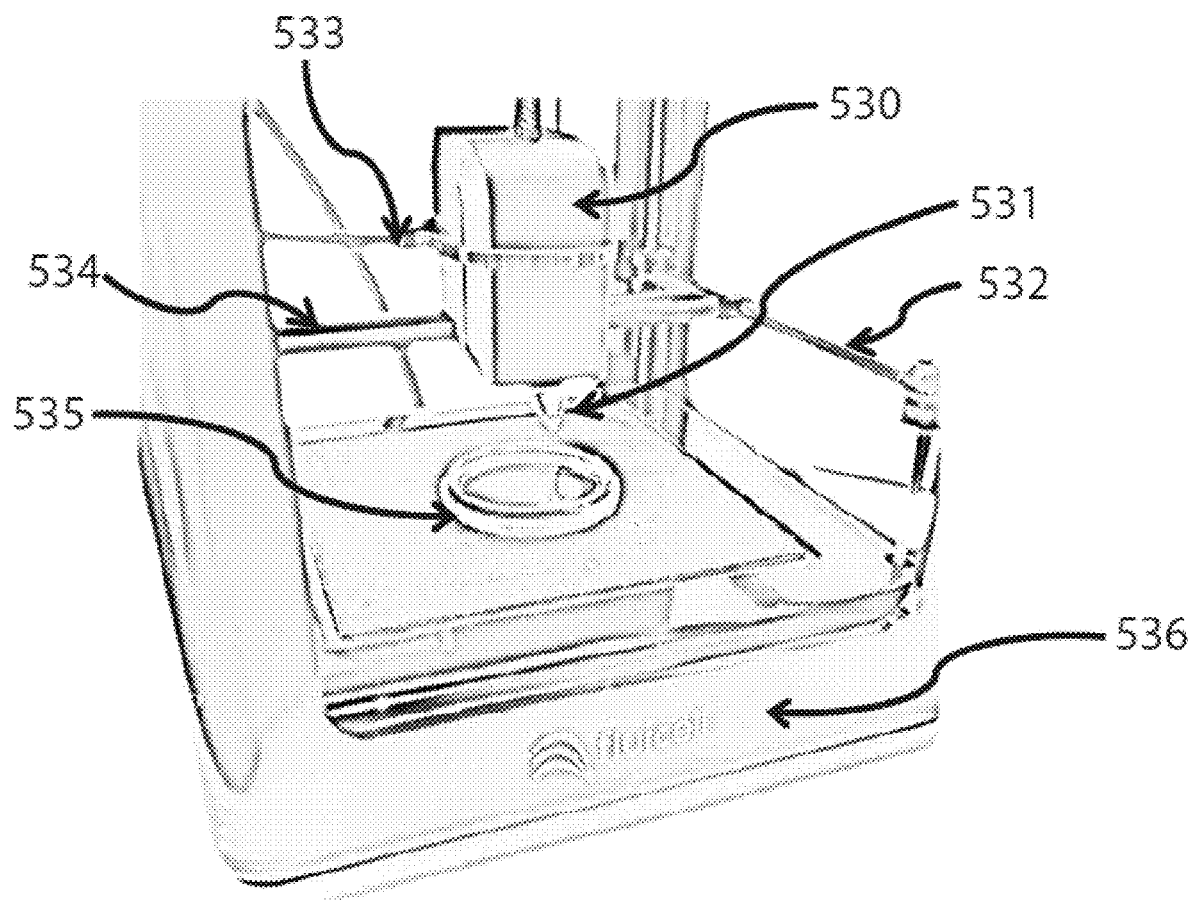
FIG. 5C depicts the 3D-positioning capabilities of an embodiment of the print head and holder, while maintaining connection to an embodiment of the control interface.
Figure 6A:
FIGS. 6A-6F depict possible cell deposition combinations onto a surface.
Figure 6B:
Figure 6C:
Figure 6D:
Figure 6E:
Figure 6F:
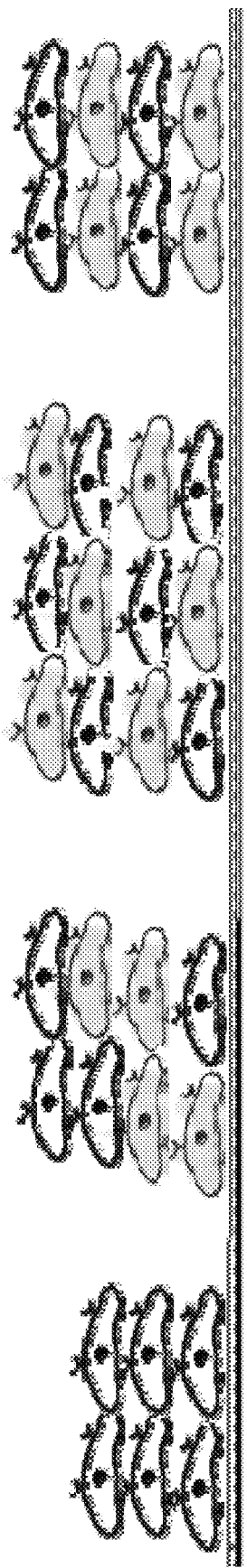

FIG. 5C depicts the integrated printing system, containing microfluidic print-head 531, which can be loaded with solutions and held in the holder 530. Holder can further contain electrical and optical sensors, imagining components, pneumatic control system, in order to operate the print-head, determine the exact position of the print-head relative to the substrate 535, and monitor the cell deposition process. The holder 530 can be translated in all three axis along rods 531, 533 and 534. Furthermore housing can contain some of the control and monitoring functions, feedback sensors and mechanism to translate the holder.

In various embodiments, the device comprises reservoirs for recirculating fluid that are adapted to receive a liquid comprising a plurality of cells. In various embodiments, the plurality of cells may be cells of any type appropriate for the practice of the herein disclosed method.

Exemplary Cell Deposition

Cell deposition can be accomplished via manual or automated positioning and actuation of fluid flows. Automated control can be accomplished via predetermined fluid delivery protocols and positioning.

The quanta of cells being dispensed can be controlled by the cell concentration in the fluid flow and can be modulated by mixing of flows within the microfluidic device.

Modulation of the recirculation zone size, e.g., by generating a pulsed flow, can modulate the cell deposition area and number of cells. For example, increasing the recirculation zone size beyond a size that permits complete recirculation can cause cells to be ejected, precipitated, or otherwise exit from the recirculating fluid and deposited in a desired location.

Figure 12:
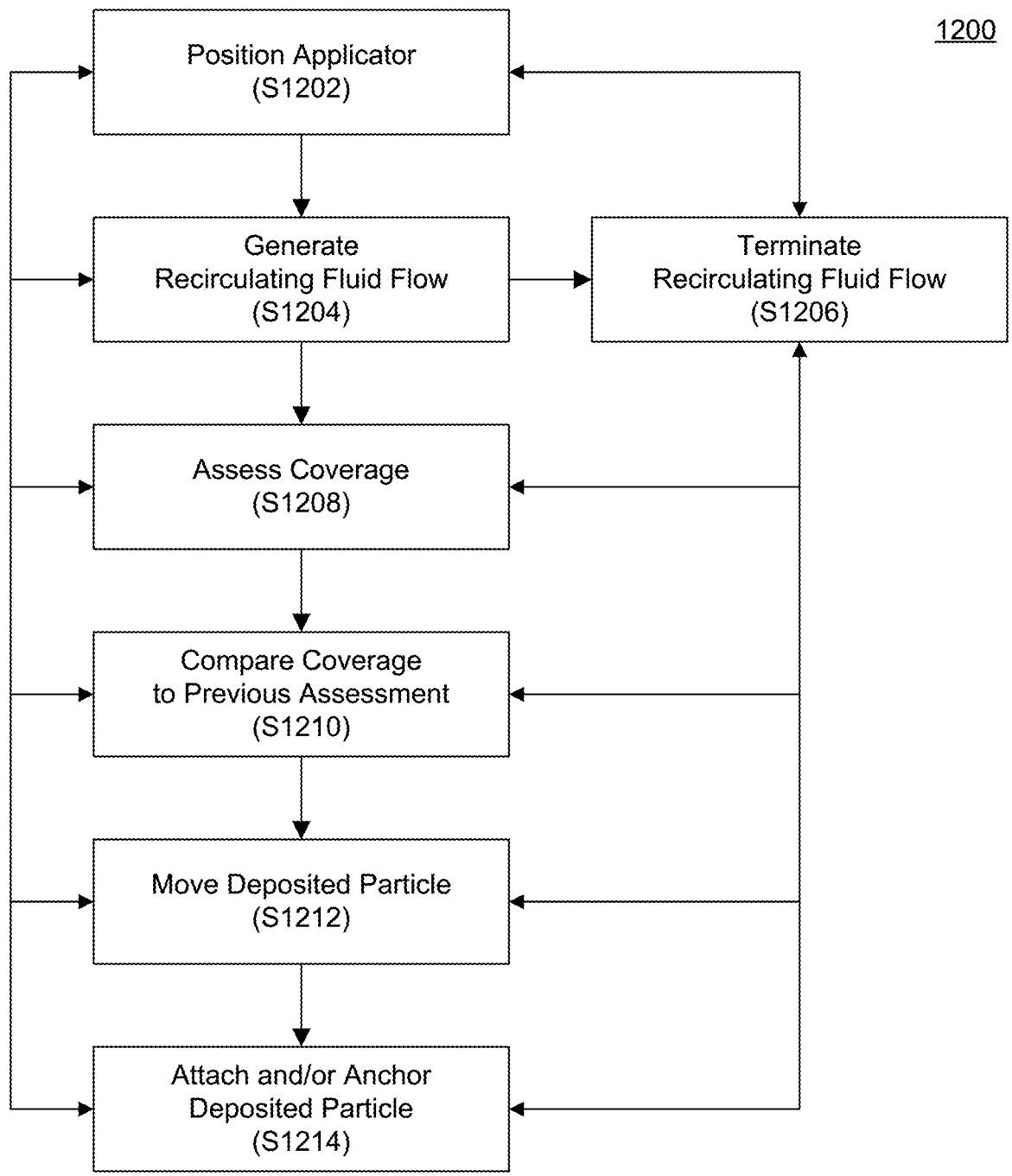
FIG. 12 depicts a method according to an embodiment of the invention.

Referring now to FIG. 12, embodiments of the invention can deposit specified quantities of cells in a desired location.

In step S1202, a recirculating fluid flow actuator and/or substrate can be positioned in a desired position relative to each other. The desired location can be manually specified or can be defined, for example, by .stl (STereoLithography) CAD files. These files represent the geometric configuration of a computer-aided design (CAD) model in thin layers. Each layer, when stacked together forms a three-dimensional model.

In some embodiments, the actuator is translated over a substrate. In other embodiments, the substrate is moved relative to a fixed actuator. The latter embodiment, may be particularly preferable when the recirculating fluid flow actuator is associated with various coverage assessment tools as described herein.

In step S1204, the actuator can be controlled to generate a recirculating fluid flow over a substrate. The substrate can be a stage upon which a structure is built. For example, the substrate can be a flat surface, a patterned surface, a microfabricated surface, a surface having regions supporting cell adhesion surrounded by regions avoiding cell adhesion, chemically or physically treated and patterned surface, a vessel having walls, a mold defining various shapes, and the like. Likewise, the substrate can also be a previously-deposited cell layer, e.g., when deposition advances in the z (axial) direction after depositing a layer. The substrate could also be biological tissue, tissue section, tissue construct, skin, hair, hair follicle, cornea, and the like. These tissues can be isolated or still associated with the organism from which they came, e.g. dermal layer on an arm, exposed cornea in an eye, and the like. Substrate can have various properties in order to achieve a desired result. For example, substrate can have non-stick properties (e.g., through coatings such as PTFE), hydrophobicity, hydrophilicity, textures, release agents, binding agents, impregnation agents and the like.

The recirculating fluid flow can emerge and be withdrawn from a device as described herein. In one embodiment, the fluid exits and is returned to separate fluid reservoirs. In another embodiment the fluid exits the device and returns to the same fluid reservoir.

In step S1208, substrate coverage is assessed. Coverage can include (i) the amount of contact between a fluid being dispensed and the substrate and/or (ii) the amount of contact between a suspended particle and the substrate. For example, the arrangement (e.g., orientation) and/or location of a particular cell can be compared to a desired location.

Coverage assessment can be performed while the recirculating fluid flow is generated or can be performed after the fluid flow is terminated in step S1206. For example, the recirculating fluid flow can be applied in step S1204 until the desired coverage is achieved in step S1208. In another embodiment, the recirculating fluid flow is applied in step S1204 and terminated in step S1206 before coverage is assessed. This loop can be repeated until the desired coverage is achieved.

Coverage can be assessed through a variety of techniques and devices. By way of non-limiting example, coverage may be assessed by optical assessment, particle tracking, by measuring conductivity and/or impedance, by ultrasound and/or by optical phase retardation measurements. A person of skill in the art will appreciate that different techniques for measuring coverage are more or less appropriate based on circumstances including, for example, the cell type and the type of liquid or liquids used.

In one embodiment, optical assessment can be performed using a digital camera (e.g., a charge-coupled device (CCD) or complementary metal oxide semiconductor (CMOS) image sensor), which can optionally be associated with various optics such as microscope, a light source, and the like. Suitable imaging modalities such as reflection, absorption, phase retardation, polarization, fluorescence, phosphorescence, and the like. Image processing can be performed on the captured image and examined to determine if the current coverage state is acceptable (e.g., in view of the .stl source file). Various patterns can place the same or similar cells adjacent to each other, place different cells adjacent to each other, place cells adjacent to non-cellular materials such as polymeric scaffolds, and the like.

In another embodiment, suspended particles are tracked, e.g., after exiting from the microfluidic print-head. For example, sperm tracking technology such as described in U.S. Patent Application Publication No. 2017/0109879 can be applied to track a plurality of moving suspended particles. The fluid flow can be modified or paused in order to facilitate desired placement of the suspended particle(s).

In another embodiment, conductivity and/or impedance can be utilized to assess coverage. For example, two or more electrodes can be positioned in the deposition chamber, at least one of which should be adjacent to the microfluidic print-head, and current can be applied between the electrodes. Without being bound by theory, Applicant believes that resistance will increase in measurements during recirculating fluid flow as cells are deposited. Likewise and without being bound by theory, Applicant believes that the presence of deposited cells after cessation of the recirculating fluid flow will result in decreased impedance. Result-indicative conductivity and/or impedance values can be determined experimentally for particular embodiments, stored in computer-readable media, and referenced in a particular embodiment.

In still another embodiment, acoustic waves (e.g., ultrasound waves) can be utilized to detect the presence and position of a recirculating fluid flow and/or a deposited particle.

In yet another embodiment, deposited particle position and/or surface coverage may be determined by optical phase retardation measurements. Any source of polarized light and as well as any technique for phase detection, such as digital holographic microsopy (DHM) may be employed.

In step S1210, an assessment (e.g., an image or measurement) can be compared to a previous assessment. For example, the deposition of a particle may produce a change relative to a previous measurement.

Figure 13:
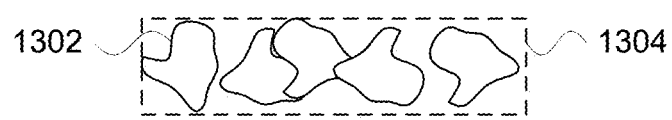
FIG. 13 is a schematic of deposited particles covering a 2-dimensional space.

The assessment can additionally or alternatively can be compared to a pre-defined threshold. For example and referring to FIG. 13, the percentage of coverage by deposited particles 1302 within a two-dimensional space 1304 (e.g., defined by a .stl file) can be measured. Exemplary thresholds include at least about 10%, at least about 25%, at least about 50%, at least about 75%, at least about 90%, at least about 99%, and 100%.

In step S1212, one or more deposited particles can be moved to a desired location. For example, the deposited particle can be pushed or pulled with; fluid flow, a physically manipulated probe, optical tweezers, pressure change, optical pulses, acoustic pulses, vibrations and the like.

In step S1214, one or more deposited particles can be attached and/or anchored to the substrate. Examples of attaching include, protein-protein interactions (e.g., biotin: avidin), bridging ions, cell adhesion proteins, degradation/denaturing proteins, polyhistidine tags, ionic interactions (e.g., adhesion of cells to surfaces coated with polylysine). In various embodiments, the deposited particles may attach to the substrate through one or more mechanism of action, including but not limited to sedimentation, Van der Waals forces, ionic and protein-protein interactions.

In various embodiments, deposited cells may anchor or be anchored to the substrate or to other cells. Examples of anchoring include curing, polymerization, cross-linking, photoisomerisation, thiol/disulphide linkages, or click chemistry.

In various embodiments, activation may include the removal of caging compounds of small molecule protecting groups, which could be associated to the plasma membrane or its associated proteins. In various embodiments, activation may include transitioning the cells from a dormant state or changing a metabolic cycle.

For example, embodiments of the invention can generate and/or apply a suitable wavelength of irradiation (e.g., ultraviolet light) to induce or promote a desired reaction (e.g., polymerization, cross-linking, and the like). One exemplary ultraviolet-light generator is described in U.S. Patent Application Publication No. 2017/0072628. The irradiation can be generated locally to the recirculating device, conveyed via a waveguide (e.g., fiber optics), or applied globally to the printed structure (e.g., after deposition of each layer).

As depicted in FIG. 12, method 1100 can repeat a plurality of times. In various embodiments, after fluid flow is terminated in S1206, it is reestablished in a second step S1204. When returning to step S1204 the recirculating fluid may be the same or different as in the previous iteration of this step. The material deposited can remain constant or change at various locations. A variety of exemplary fluids for deposition will be described herein. For example, scaffolding materials can first be deposited followed by cells and vice versa. In some embodiments, both the recirculating fluid and the plurality of cells may be the same as the previous iteration or may independently be different from the previous iteration. In other embodiments, the reestablished recirculating fluid flow may contain a plurality of distinct suspended cells. These cells may be distinct from the first plurality of suspended cells in any way that would be appreciated by a person of skill in the art. By way of non-limiting example, the distinct plurality of suspended cells may be a second cell type or may be the same cell type, but may carry a different gene or set of genes or may have been exposed to a different set of external stimuli than the first plurality of suspended cells such as various chemokines, cytokines, ligands or other signaling molecules.

In various embodiments, the recirculating fluid may be a second solution that can be the same or different from the first solution. By way of non-limiting example, the first and second solution may independently be media, gel, an aqueous solution or a polymer solution.

Media that may be appropriate for use in various embodiments of the invention includes but is not limited to: physiological media, growth media such as DMEM, MEM, Hams F10, Hams F12, selective media such as eosin methylene blue and Sabouraud's agar, differential media such as MacConkey agar and blood agar, binding media such as cell ink media and cell glue media, as well as transport media such as thioglycolate broth and Venkataraman Ramakrishna medium. Gels that may be appropriate include: Agar agarose, gelatin and collagen. Polymeric solutions that may be include Poly(N-isopropylacrylamide) (PNIPAM).

In various embodiments, supplemental liquid may be introduced into the area of recirculation from channel exits exiting the tip of the device, exiting in the sides of the device, or through auxiliary channels running parallel to the device, or by fluidic outlets directed to the vicinity of the recirculation volume.

In another aspect, the invention provides a method for cell deposition by: (a) generating a recirculating flow from a flow confinement device over a substrate, the recirculating flow comprising a first liquid and a first plurality of suspended cells within the first liquid, the flow confinement device comprising a plurality of channels; and (b) switching between (a) and at least one of: continuing the recirculating flow over the substrate for a duration until a desired quanta of cells has been released from the flow confinement device; slowing down, modulating, or discontinuing the recirculating flow over the substrate for a duration until a desired quanta of cells has been released from the flow confinement device; discontinuing the recirculating flow by altering pressure balance between one or several channels such that there is net positive pressure leading to that liquid and materials contained in said liquid are injected into the environment over the substrate and not flowing back to the flow confinement device for a duration until a desired quanta of cells has been released from the flow confinement device; discontinuing the recirculating flow by altering pressure balance between one or several channels such that there is no pressure difference between device and its surrounding leading to the recirculating flow being dispensed into the environment over the substrate and not flowing out of the flow confinement device and not flowing back to the flow confinement device for a duration until a desired quanta of cells has been released from the flow confinement device; discontinuing the recirculating flow by altering pressure balance between one or several channels such that there is net negative pressure leading to that liquid and materials contained in said liquid are flowing back into the flow confinement device for a duration until a desired quanta of cells has been removed from the environment or the substrate/surface back into the flow confinement device. Steps (a) and (b) can be continued for an arbitrary period of time.

In various embodiments the method may also be practiced where the recirculating flow is on the substrate.

The method may be practiced by switching between (a) and (b) or among the various flow modes recited in (b) at the discretion of the operator. In various embodiments, the flow mode may be changed one, two, three, four five or more times over the course of the method. In various embodiments, the method may be practiced under manual control by an operator or under the control of a preprogrammed flow controller.

In various embodiments, the cells released from the flow confinement device are deposited on a substrate. In various embodiments, the cells released from the flow confinement device are deposited and adhere to a substrate. When the cells adhere, they may do so by anchoring or attaching.

By way of non-limiting example, the method may include: (a) generating a recirculating flow from a flow confinement device over a substrate, the recirculating flow comprising a first liquid and a first plurality of suspended cells within the first liquid; and (b) continuing the recirculating flow over the substrate for a duration until a desired quanta of cells has been released from the flow confinement device.

By way of non-limiting example, the method may include: (a) generating a recirculating flow from a flow confinement device over a substrate, comprising a first liquid and a first plurality of suspended cells within the first liquid, wherein the recirculating flow is in contact with said substrate; and (b) continuing the recirculating flow over the substrate for a duration until a desired quanta of cells has been released from the flow confinement device.

By way of non-limiting example, the method may include: (a) generating a recirculating flow from a flow confinement device over a substrate, the recirculating flow comprising a first liquid and a first plurality of suspended cells within the first liquid; and (b) slowing down, modulating, or discontinuing the recirculating flow over the substrate for a duration until a desired quanta of cells has been released from the flow confinement device.

By way of non-limiting example, the method may include: (a) generating a recirculating flow from a flow confinement device over a substrate, the recirculating flow comprising a first liquid and a first plurality of suspended cells within the first liquid, wherein the recirculating flow is in contact with said substrate; and (b) slowing down, modulating or discontinuing the recirculating flow over the substrate for a duration until a desired quanta of cells has been released from the flow confinement device.

By way of non-limiting example, the method may include: (a) generating a recirculating flow from a flow confinement device over a substrate, the flow confinement device, the flow confinement device comprising a plurality of channels, the recirculating flow comprising a first liquid and a first plurality of suspended cells within the first liquid; and (b) discontinuing the recirculating flow by altering pressure balance between one or several channels such that there is net positive pressure leading to that liquid and materials contained in said liquid are injected into the environment over the substrate and not flowing back to the flow confinement device for a duration until a desired quanta of cells has been released from the flow confinement device.

By way of non-limiting example, the method may include: (a) generating a recirculating flow from a flow confinement device, the flow confinement device comprising a plurality of channels, over a substrate, comprising a first liquid and a first plurality of suspended cells within the first liquid, wherein the recirculating flow is in contact with said substrate; and (b) discontinuing the recirculating flow by altering pressure balance between one or several channels such that there is net positive pressure leading to that liquid and materials contained in said liquid are injected into the environment over the substrate and not flowing back to the flow confinement device for a duration until a desired quanta of cells has been released from the flow confinement device.

By way of non-limiting example, the method may include: (a) generating a recirculating flow from a flow confinement device, the flow confinement device comprising a plurality of channels, over a substrate, the recirculating flow comprising a first liquid and a first plurality of suspended cells within the first liquid; and (b) discontinuing the recirculating flow by altering pressure balance between one or several channels such that there is no pressure difference between device and its surrounding leading to the recirculating flow being dispensed into the environment over the substrate and not flowing out of the flow confinement device and not flowing back to the flow confinement device for a duration until a desired quanta of cells has been released from the flow confinement device.

By way of non-limiting example, the method may include: (a) generating a recirculating flow from a flow confinement device, the flow confinement device comprising a plurality of channels, over a substrate, the recirculating flow comprising a first liquid and a first plurality of suspended cells within the first liquid and is in contact with said substrate; and (b) discontinuing the recirculating flow by altering pressure balance between one or several channels such that there is no pressure difference between the flow confinement device and surroundings, leading the recirculating flow being dispensed into the environment over the substrate and not flowing out of the fluid flow applicator and not flowing back to the fluid flow applicator for a duration until a desired quanta of cells has been released from the flow confinement device.

By way of non-limiting example, the method may include: (a) generating a recirculating flow from a flow confinement device, the flow confinement device comprising a plurality of channels, over a substrate, the recirculating flow comprising a first liquid and a first plurality of suspended cells within the first liquid; (b) discontinuing the recirculating flow by altering pressure balance between one or several channels such that there is net positive pressure leading to the recirculating flow being injected into the environment over the substrate and not flowing back to the flow confinement device for a duration until a desired quanta of cells has been released from flow the confinement device; and (c) altering pressure balance between one or several channels such that there is no pressure difference between the device and its surroundings leading to the recirculating flow being dispensed into the environment over the substrate and not flowing out of the flow confinement device and not flowing back to the flow confinement device for a duration until a desired quanta of cells has been released from the flow confinement device, wherein in various embodiments the flow confinement device is switched between (a), (b), and (c) in arbitrary sequence for arbitrary periods of time.

By way of non-limiting example, the method may include: (a) generating a recirculating flow from a flow confinement device over a substrate, the recirculating flow comprising a first liquid and a first plurality of suspended cells within the first liquid, the flow confinement device comprising a plurality of channels; and (b) discontinuing the recirculating flow by altering pressure balance between one or several channels such that there is net negative pressure leading to that liquid and materials contained in said liquid are flowing back into the flow confinement device for a duration until a desired quanta of cells has been removed from the environment or the substrate/surface back into the flow confinement device, wherein in various embodiments the flow confinement device is switched between (a) and (b), in arbitrary sequence for arbitrary periods of time.

In various embodiments, the cells released from the flow confinement device are deposited to a first location on volume element, substrate, or surface, and then are moved by the flow confinement device to another location. For various applications, it may be advantageous to move cells to a new location after an initial deposition, either to correct an error or in response to measurements. By way of non-limiting example, a measurement of cell quanta may determine that more cells than intended were deposited. The deposited cells may be moved to a new location by a variety of methods. By way on non-limiting example, pressure from the recirculating fluid flow may adjust the position of the cells or the cells may be resuspended in the recirculating fluid and the flow confinement device may be moved to a new location for deposition. In various embodiments, similar techniques may be used to remove cells from the substrate.

In various embodiments, the cells released from the flow confinement device are deposited at a first location on the substrate, and then are moved by cellular migration to another location on the substrate. In various embodiments, the cellular migration takes place by chemotaxis. In various embodiments, the cells are moved by movement (e.g., filipod movement) driven by chemotaxis, immune cell migration driven by chemokine and cytokine release or by cell migration in blood stream, lymph stream or cerebrospinal fluid (CSF) stream.

Additions to Living Organisms

Embodiments of the invention can be applied to add material to living organisms. In such embodiments, the organism can be considered the substrate. Such embodiments can be used for a variety of therapeutic and/or cosmetic applications including regenerative medicine, tissue grafting, plastic surgery, orthopedics, and the like.

Embodiments of the invention utilizing a soft print-head are particularly advantageous in such embodiments, especially when applied to delicate tissues such as the eye and the ear.

Such an in-situ-generated graft can be bound to the organism through various techniques including the use of cross-linking as discussed herein.

In-situ-generated grafts can also be used for research purposes. For example, cancer cells can be printed within an organism (e.g., in a predefined and consistent pattern across multiple organisms) for experimental animal research.

System for Cell Dispensation Utilizing Confined Recirculating Fluid

In one aspect, the invention provides a system for dispensing and printing cells and particles, including: a flow confinement device; a controller configured to generate a confined liquid volume outside the flow confinement device; and where the confined liquid volume or materials contained in said liquid volume can be released to the environment by confined, modulated, and non-confined flow modes in arbitrary sequence and for arbitrary periods of time by said controller; one or more media containing cells or cell constituents supplied into the confined liquid volume through the flow confinement device; a volume; a substrate; a positioning system configured to position the flow confinement device and therefore the confined, modulated, or non-confined liquid volume relative to the substrate, such that confined liquid volume can interact with the substrate.

The components of the system are described above. The confined liquid volume refers to the zone of flow recirculation. In certain flow modes, the recirculating flow may be terminated, thereby generating a non-confined liquid. Both confined liquids and non-confined liquids may deposit cells on the substrate, though the skilled person will appreciate that each of these modes have varying properties with respect to cell deposition and will be variously more and less suited for various applications.

The flow confinement device may be positioned over or on the surface or substrate. The distinction being drawn here is that when the flow confinement device is positioned on the substrate, the recirculating fluid touches the area for deposition. When the flow confinement device is positioned above the substrate, the recirculating fluid does not touch the area for deposition.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Figure 9A:
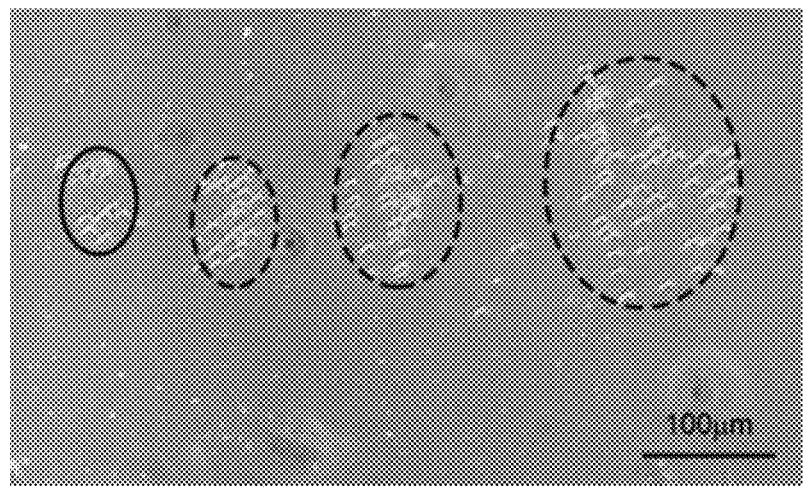
FIG. 9A depicts experimental images of *Saccharomyces-cerevisiae* deposition onto Concanavalin-A-coated glass surface. Spots of increasing size are generated in a line. The scale bar in FIG. 9A applies to all images.

Yeast cells, *Saccharomyces cerevisiae*, were printed at various spot sizes onto a primed glass surface using a continuous flow scheme (FIG. 9A). A glass bottom petridish (wilco wells) was cleaned with ethanol then dried with nitrogen. 2 ml of a 1 mg/ml Conconavalin A solution was then added to the dish and allowed to bind to the surface for 40 minutes in a 30 degree incubator. After which the Conconavalin solution was removed and washed twice with 100 mM Sodium citrate buffer solution. 5 ml of citrate solution was then added into the Petri dish as the immersion medium.

A BIOPEN® tip was used as the print head whereby three of the solution wells were filled with citrate solution and one was filled with Yeast cells in medium. The medium was a growth medium of YPD broth which was diluted in the BIOPEN® well to ½ concentration using the citrate solution. A recirculation flow of yeast cells was established in the immersion medium above the surface. The tip was then subsequently lowered to the surface to allow cells to flow over and attach to the petri dish surface. Once a sufficient number had attached the tip was raised away from the surface, translated to a new location, the pressures adjusted to give a larger recirculation zone, the lowered again to the surface. The same protocol was repeated for each subsequent printed zone of cells.

Example 2

Figure 9B:
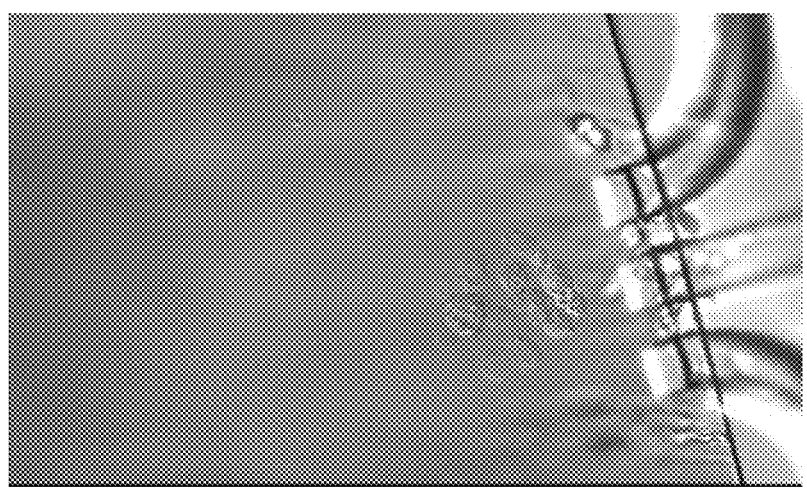
FIG. 9B depicts printing NIH 3T3 cells onto laminin-coated glass surface.

Mouse embryonic fibroblasts, NIH3T3 cells, were printed onto a primed glass surface using a continuous flow scheme (FIG. 9B). A glass bottom Petri dish (wilco wells) was cleaned with ethanol then dried with nitrogen. 2 ml of a 1 mM laminin solution was then added to the dish and allowed to bind to the surface for 30 minutes in a 37 degree incubator. After which the laminin solution was removed and washed twice with 1× (200 mM) phosphate buffered saline (PBS) solution. 5 ml of PBS solution was then added into the Petri dish as the immersion medium.

A BIOPEN® tip was used as the print head whereby three of the solution wells were filled with PBS solution and one was filled with NIH3T3 cells in medium. The medium was a growth medium of DMEM containing 10% FBS, which was diluted in the BIOPEN® well to ¼ concentration using the PBS solution. A recirculation flow of cells was established in the immersion medium above the surface. The tip was then subsequently lowered to the surface to allow cells to flow over and attach to the petridish surface.

Example 3

Figure 9C:
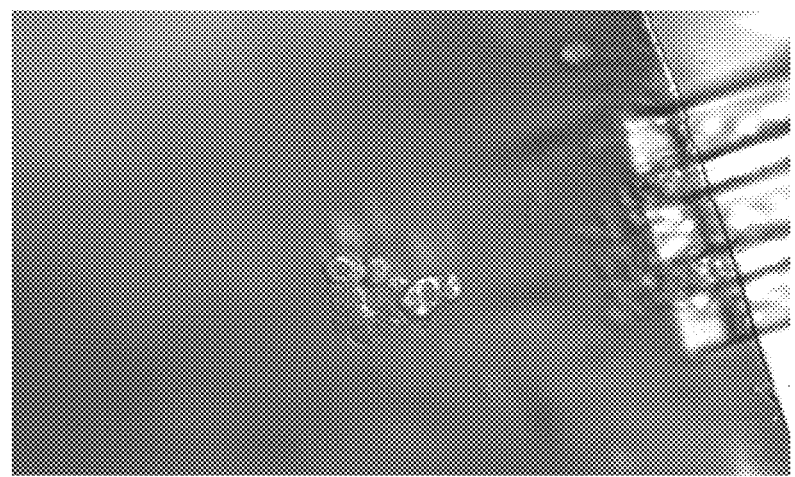
FIG. 9C depicts printing SH-SYSY cells onto poly-L-lysine-coated glass surface.

Human derived neuroblastoma cells, SH-SYSY, were printed onto a primed glass surface using a stopped flow scheme (FIG. 9C). A glass bottom Petri dish (wilco wells) was cleaned with ethanol then dried with nitrogen. 2 ml of a 0.1 mg/ml poly-1-lysine solution was then added to the dish and allowed to bind to the surface for 10 minutes in a 37 degree incubator. After which the lysine solution was removed and washed twice with 1× (200 mM) phosphate buffered saline (PBS) solution. The petridish wash the dried with nitrogen and allowed to fully dry in a bio hood for 2 hours. After fully drying, 5 ml of PBS solution was then added into the Petri dish as the immersion medium.

A BIOPEN® tip was used as the print head whereby three of the solution wells were filled with PBS solution and one was filled with SH-SYSY cells in medium. The medium was a growth medium of DMEM/F12 plus glutamine, containing 10% FBS, which was diluted in the BIOPEN® well to ¼ concentration using the PBS solution. A recirculation flow of cells was established in the immersion medium above the surface, then the tip was lowered allow begin the deposition. Solution speed was slowed once cells were ejecting for the tip and began to adhere to the surface, then stopped before removal of the tip to allow for binding.

Example 4

Figure 15C:
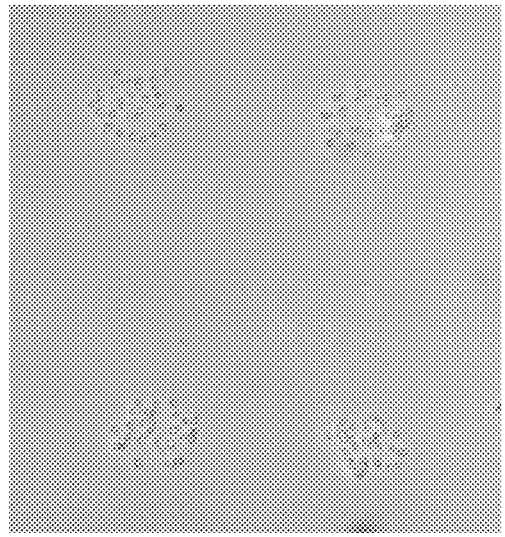
FIGS. 15A-C depict an exemplary cell deposition process of the present invention using *Saccharomyces cerevisiae* in a physiological buffer onto a Concanavalin A-coated glass surface.
Figure 15B:
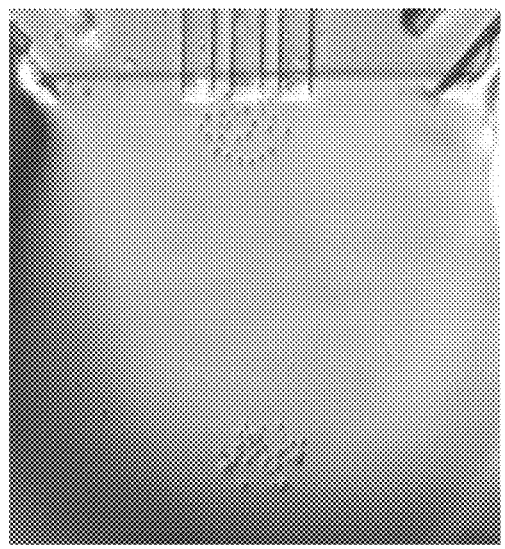
Figure 15A:
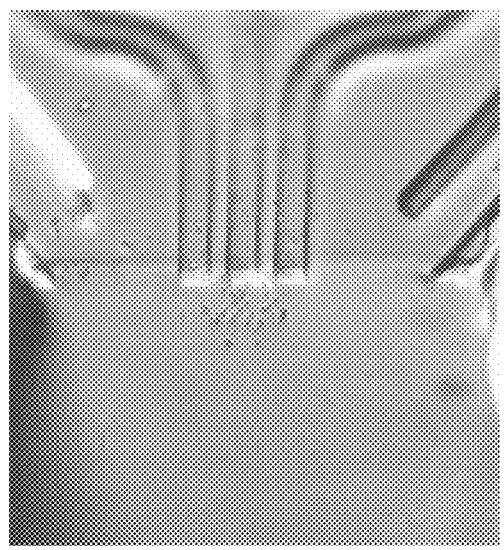
Figures 17A, 17B, 17C:
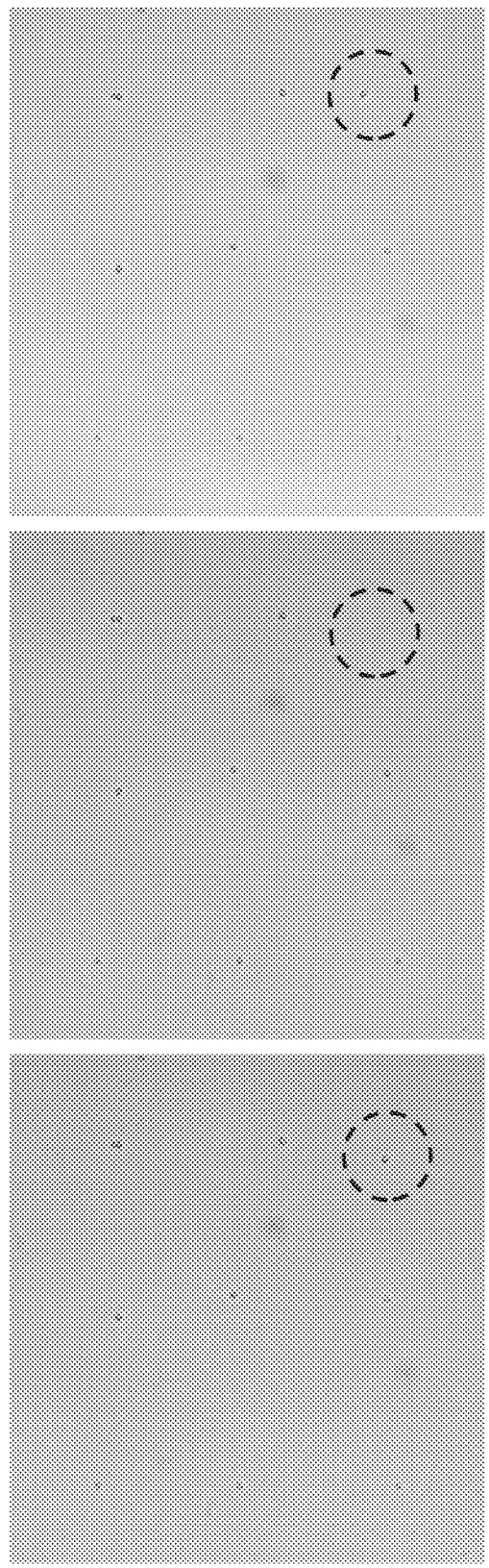
FIGS. 17A-17C illustrates the editing and rewriting a single cell array using *Saccharomyces cerevisiae*, printed in a physiological buffer onto a Concanavalin A-coated glass surface.

*Saccharomyces cerevisiae* cells were deposited onto a concanavalin A-coated glass surface using a recirculation flow above the surface (FIG. 15A). A glass surface was coated with concanavalin A, using standard techniques as understood in the art. *Saccharomyces cerevisiae* cells were prepared in a physiological buffer and printed onto the coated surface using recirculation flow as described herein. Cells were deposited in an array of adjacent spots, shown in FIGS. 15B and 15C. Results demonstrate, as depicted in FIG. 15C, that an array of spots having the same size was achieved.

Example 5

In order to further demonstrate that multiple samples can be printed onto the same spot sequentially, separate aliquots of *Saccharomyces cerevisiae* cells were deposited into the same spot on a coated glass surface (FIG. 16). A glass surface was coated with concanavalin A using standard techniques as understood in the art. *Saccharomyces cerevisiae* cells were prepared in a physiological buffer. Cells were further prepared with one of three different colored labels in order to differentiate each aliquot of the cells.

A BIOPEN® tip was used as the print head whereby three of the solution wells were filled with solutions of *Saccharomyces cerevisiae* cells in physiological buffer. Aliqouts of cells with one of each of the three labels were loaded into one of each of the three on-device wells of the print head. Cells were deposited from a first on-device well onto the coated glass surface, shown in FIG. 16A. Cells from a second on-device well were then deposited onto the same region of the glass surface as the cells from the first on-device well, shown in FIG. 16B. Cells from a third on-device well were deposited onto the same region of the glass surface as the cells from the first and second on-device well, shown in FIG. 16C. An overlay of the three aliquots of cells deposited onto the same spot is shown in FIG. 16D.

Example 6

In order to further demonstrate the printing capabilities of the system and methods of the present invention, cells were deposited onto coated glass surfaces in various deposition patterns. Glass surfaces were coated with either concanavalin A or poly-1-lysine using standard techniques as understood in the art. Cells including *Saccharomyces cerevisiae* cells (FIGS. 18A-18E), SH-SYSY (human derived neuroblastoma) cells (FIGS. 19A-19E), and MDA-MB-231 (human invasive ductal carcinoma) cells (FIGS. 20A-20E) were prepared in a physiological buffer.

Figure 19A:
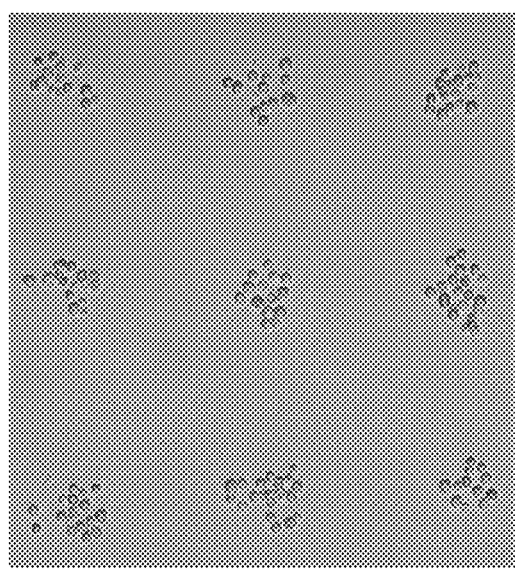
FIGS. 19A-19E depict examples of cell deposition using SH-SYSY cells (Human derived neuroblastoma cells) printed in a physiological buffer onto a poly-L-lysine-coated glass surface.
Figure 19B:
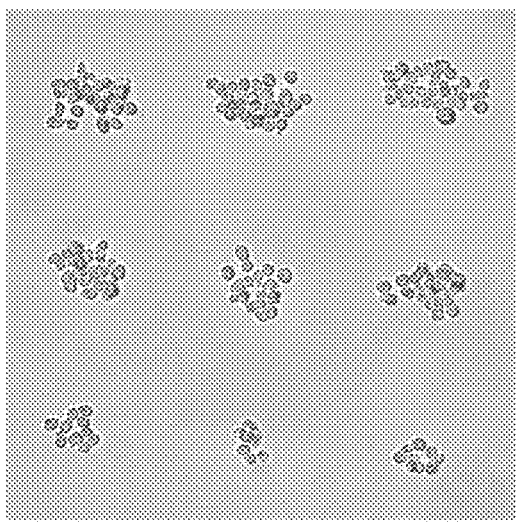
Figure 19C:
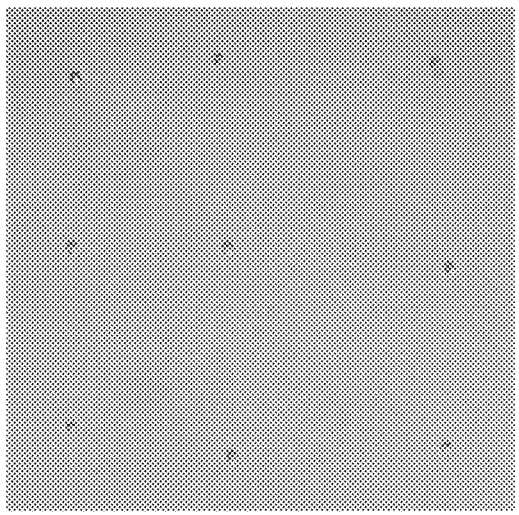
Figure 19D:
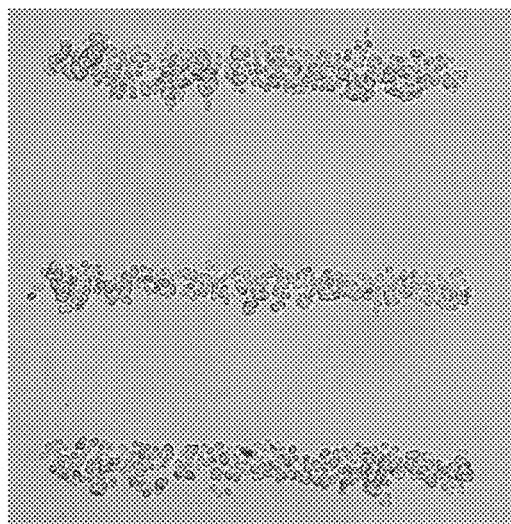
Figure 19E:
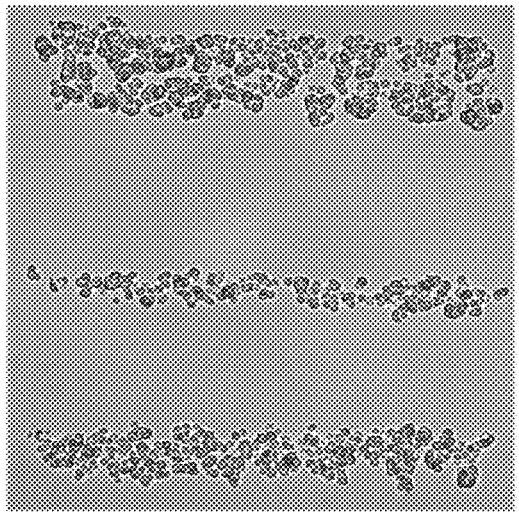
Figure 20A:
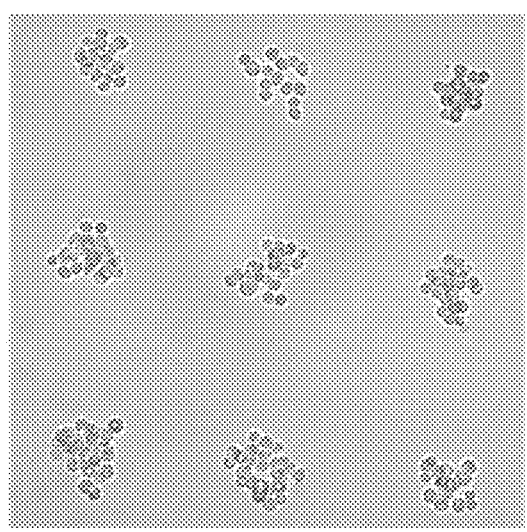
FIGS. 20A-20E depicts examples of cell deposition using MDA-MB-231 cells (Human Invasive ductal carcinoma cells) printed in a physiological buffer onto a poly-L-lysine-coated glass surface.
Figure 20B:
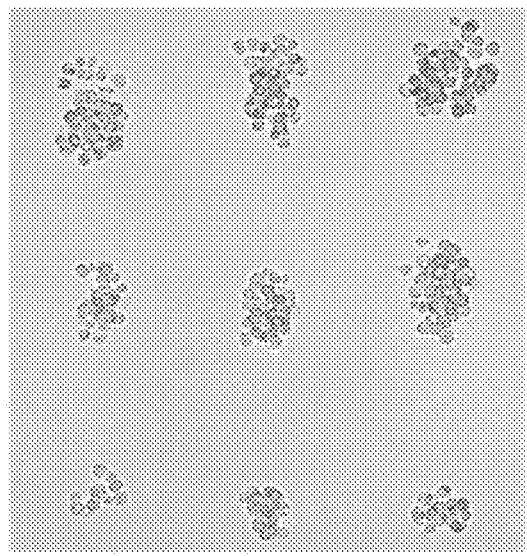
Figure 20C:
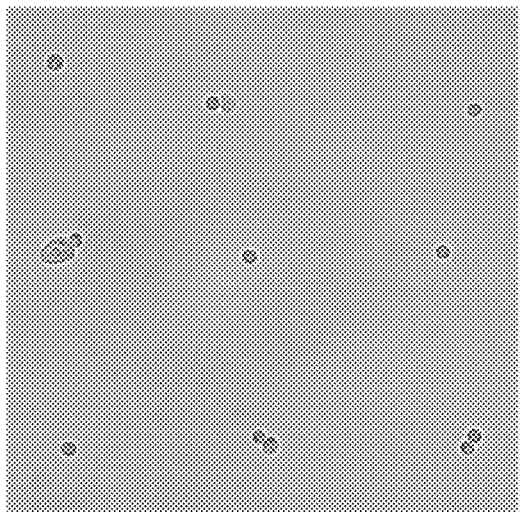
Figure 20D:
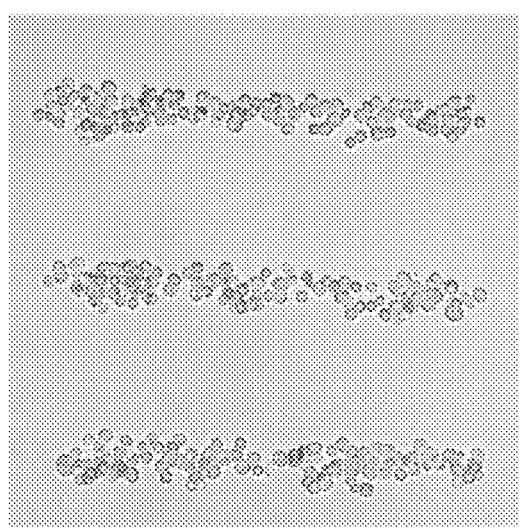
Figure 20E:
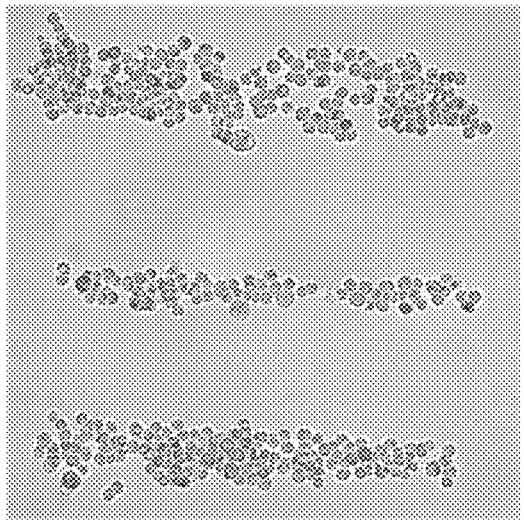

A BIOPEN® tip was used as the print head whereby one or more solution wells were filled with one or more cell types, either labeled or unlabeled, in physiological buffer. Cells were then deposited onto a coated surface in one of five patterns. The print head with on-device wells filled with one cell type was first used to deposit cells onto a surface coated with either concanavalin A (in the case of *Saccharomyces cerevisiae* cells) or poly-L-lysine (in the case of SH-SYSY and MDA-MB-231 cells). Cells were deposited in an array of spots having approximately the same size (FIGS. 18A, 19A, and 20A), and array of spots having different sizes (FIGS. 18B, 19B, and 20B), an array of single cells (FIGS. 18C, 19C, and 20C), in a series of lines having the same width, (FIGS. 18D, 19D, and 20D), or in a series of lines having different widths (FIGS. 18E, 19E, and 20E).

Figure 21A:
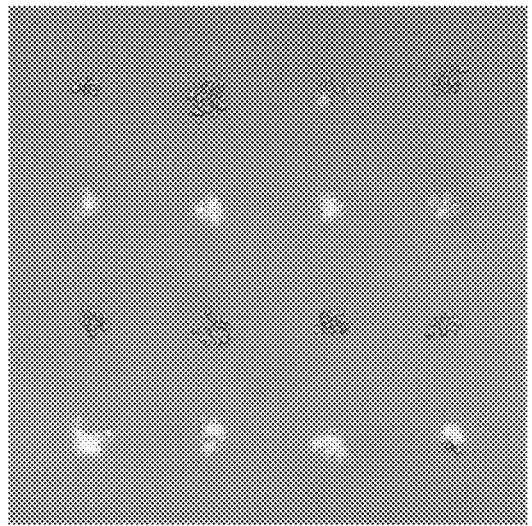
FIGS. 21A-21D depict examples of cell deposition using two different types of cells in the same device, where the cells are printed in a physiological buffer onto a poly-L-lysine-coated glass surface. Cell type 1 is MDA-MB-231, labeled dark. Cell type 2 is SH-SYSY, labeled white.
Figure 21B:
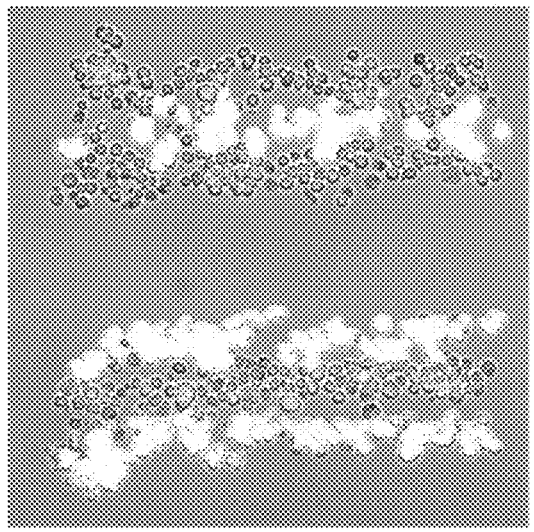
Figure 21C:
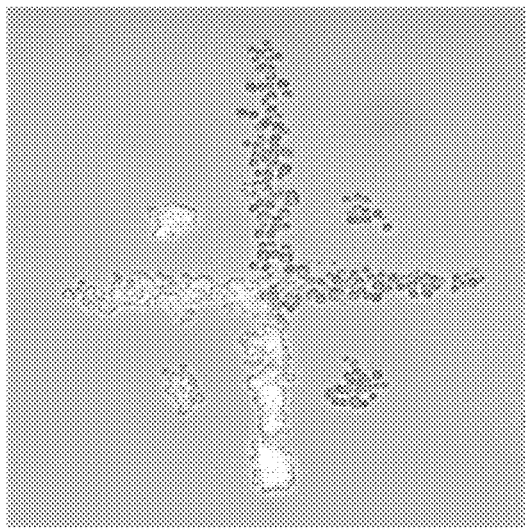
Figure 21D:
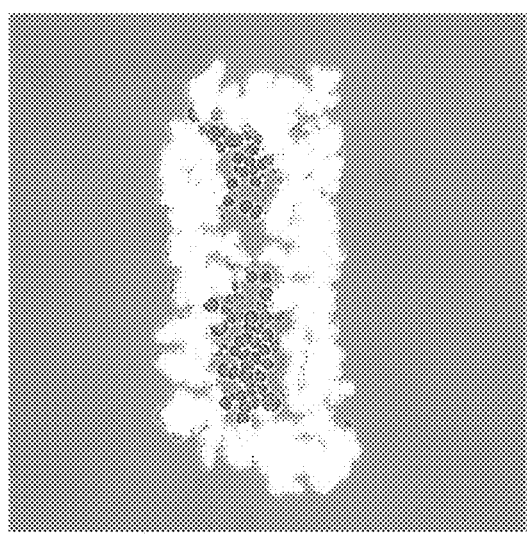

Next, a BIOPEN® tip was used to print two different cell types in the same device. One solution well was filled with a first cell type, labeled Cell Type 1 (MDA-MB-231 cells), and another on-device well with filled with a second cell type, labeled Cell Type 2 (SH-SYSY cells). Cells were deposited in one of four patterns, including: a 4×4 spot array of spots having the same size and alternating between cell type 1 and cell type 2 (FIG. 21A); an array of nestle stripes of the two cell types (FIG. 21B); a combination of a cross and spot pattern including the two cell types (FIG. 21C); and a patterned region wherein one cell type encloses the other cell type in that region (FIG. 21D).

Figure 22B:
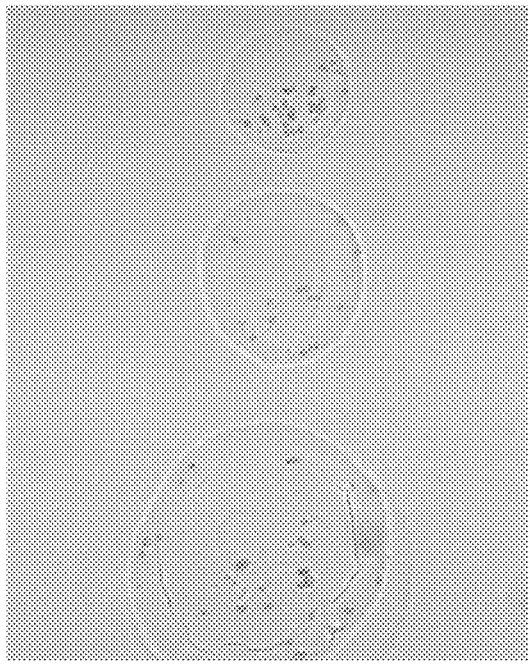
FIGS. 22A-22D depicts examples of cell deposition using a gel matrix where the cells are printed in air onto a glass surface. Cell type 1 is *Saccharomyces cerevisiae* and is dark. Cell type 2 is A431 Epidermoid carcinoma and is light.
Figure 22D:
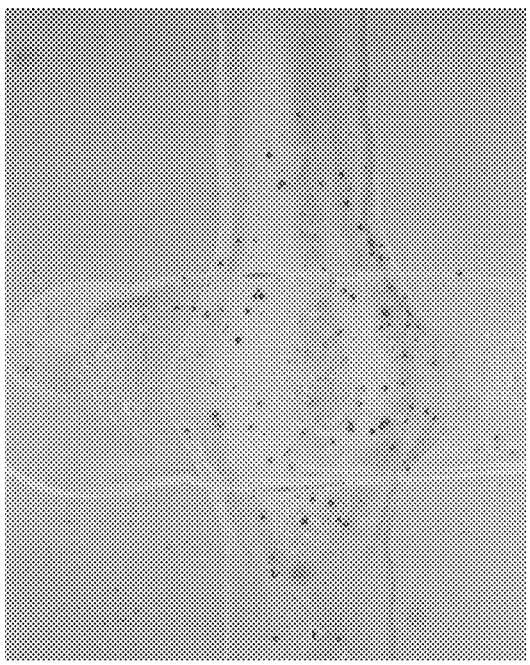
Figure 22A:
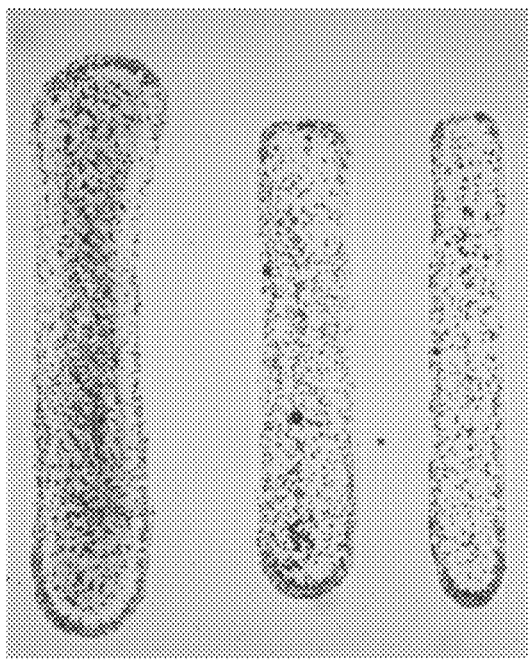
Figure 22C:
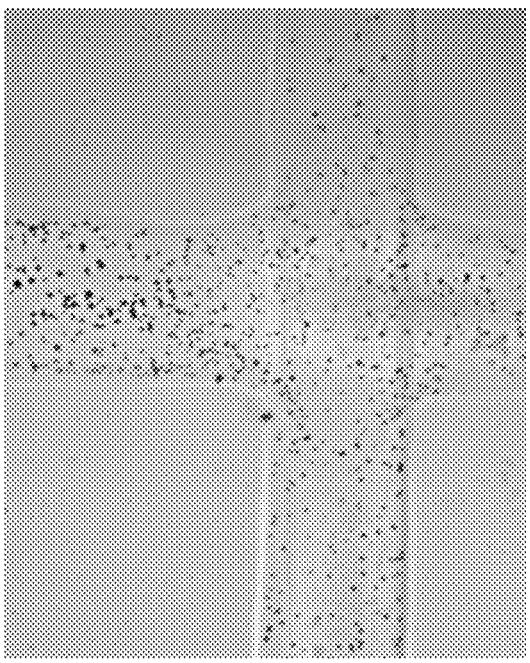

A BIOPEN® tip was then used to deposit cells into a gel matrix on a glass surface. Cells, including *Saccharomyces cerevisiae* cells and A431 epidermoid carcinoma cells were loaded into one of the on-device wells. In certain embodiments, one of each cell type was loaded in the same or similar concentrations into each well. In other embodiments, varying concentrations of a given cell type were loaded into each well. As shown in FIG. 22, cells were deposited in a pattern into a gel matrix. Cells were patterned in either lines having different widths (FIG. 22A), spots having different sizes (FIG. 22B), or in layered lines (FIGS. 22C and 22D). Alternatively, cells were deposited as a spot into a region of the gel matrix forming a cell-embedded region, shown in FIG. 23. Cells were deposited as a spot of a single cell type forming a single cell type embedded region (FIGS. 23A and 23C) or a spot of more than one cell type was deposited into the same spot in the gel matrix, forming a mixed cell embedded region (FIG. 23B). Cells were sequentially or repeatedly spotted into the gel matrix in order to generate cell-embedded regions having varying cell ratios. In certain cases, cells were deposited from wells having different concentrations of cells in order to generate cell-embedded regions having varying cell ratios of one or more cell types (FIG. 23D).

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method comprising:
(a) generating a recirculating flow from a flow confinement device over a substrate, the recirculating flow comprising a liquid and a first plurality of suspended cells within the liquid, the flow confinement device comprising a plurality of channels, wherein generating further includes monitoring a quanta of cells being released from the flow containment device; and
(b) switching between (a) and at least one of:
continuing the recirculating flow over the substrate for a duration until a desired quanta of cells has been released from the flow confinement device;
slowing, modulating, or discontinuing the recirculating flow over the substrate for a duration until a desired quanta of cells has been released from the flow confinement device;
discontinuing the recirculating flow by altering pressure balance between one or several channels such that there is net positive pressure leading to that liquid and materials contained in said liquid are injected into the environment over the substrate and not flowing back to the flow confinement device for a duration until a desired quanta of cells has been released from the flow confinement device;
discontinuing the recirculating flow by altering pressure balance between one or several channels such that there is no pressure difference between the device and its surrounding leading to the recirculating flow being dispensed into the environment over the substrate and not flowing out of the flow confinement device and not flowing back to the flow confinement device for a duration until a desired quanta of cells has been released from the flow confinement device; and
discontinuing the recirculating flow by altering pressure balance between one or several channels such that there is net negative pressure leading to that liquid and materials contained in said liquid are flowing back into the flow confinement device for a duration until a desired quanta of cells has been removed from the environment or the substrate back into the flow confinement device;

wherein:
(a) and (b) are repeatedly performed using a first liquid and a first plurality of cells within the first liquid so as to form a first layer of cells on the substrate when the substrate is covered by the first liquid;
(a) and (b) are furthermore repeatedly performed using a second liquid and a second plurality of cells within the second liquid so as to form a second layer of cells on the first layer of cells when the substrate is covered by the second liquid;
the first plurality of cells is of a different type than the second plurality of cells; and
the flow containment device is not in direct contact with the substrate.

2. The method according to claim 1, wherein the cells released from the flow confinement device are deposited on the substrate.

3. The method of claim 1, wherein the cells released from the flow confinement device are deposited on and adhere to the substrate.

4. The method of claim 1, wherein the cells released from the flow confinement device are deposited to a first location on the substrate, and then are moved by the flow confinement device to another location.

5. The method of claim 1, wherein the cells released from the flow confinement device are deposited to a first location on the substrate, and then are removed by flow confinement device.

6. The method of claim 1, wherein the substrate is translated in 3D relative to the flow confinement device using an electronically controlled positioning device.

7. The method of claim 1, wherein the specified quantum of cells is a layer of adjacent cells having a specified threshold of coverage over a two-dimensional field.

8. The method of claim 1, wherein the recirculation zone size is pulsed larger to exceed the flow confinement to modulate the cell deposition area and number of cells released.

9. The method of claim 1, wherein the quanta of cells being dispensed can be controlled by the duration of the fluid flow modulated by mixing of flows within the flow confinement device.

10. The method of claim 1, wherein the quanta of cells being dispensed can be controlled by the distance the flow confinement device is from the substrate.

11. The method of claim 1, wherein the first liquid and the second liquid have the same composition.

12. The method of claim 1, wherein the method further comprises: assessing whether one or more of the cells attaches to the substrate.

13. The method of claim 12, wherein the assessing step further comprises measuring surface coverage.

14. The method of claim 13, wherein measuring surface coverage includes performing one or more selected from the group consisting of: visual observation, particle and object tracking from images, conductivity measurement, impedance measurement, fluorescence intensity measurement, optical density, phase retardation measurement, and acoustic wave sensing.

15. The method of claim 14, further comprising:
measuring the substrate after step (a);
comparing this measurement to a reference value measured before step (a); and detecting whether the specified quantum of cells is present relative to the reference measurement.

16. The method of claim 1, further comprising:
repeating steps (a) and (b) with a further recirculating flow, wherein the further recirculating flow contains a further plurality of suspended cells.

17. The method of claim 16, wherein the further recirculating flow is selected from the group consisting of: a cell binding medium, a membrane poration medium, an activating medium, a cell killing medium, and a releasing medium.

\* \* \* \* \*